United States Patent
Hnat

(10) Patent No.: US 11,872,199 B2
(45) Date of Patent: Jan. 16, 2024

(54) TOPICAL FORMULATIONS OF CYCLOOXYGENASE INHIBITORS AND THEIR USE

(71) Applicant: SMARTECH TOPICAL, INC., Santee, CA (US)

(72) Inventor: Thomas Hnat, San Diego, CA (US)

(73) Assignee: SMARTECH TOPICAL, INC., Santee, CA (US)

( * ) Notice: Subject to any disclaimer, the term of this patent is extended or adjusted under 35 U.S.C. 154(b) by 0 days.

(21) Appl. No.: 18/152,034

(22) Filed: Jan. 9, 2023

(65) Prior Publication Data
US 2023/0233495 A1  Jul. 27, 2023

Related U.S. Application Data

(63) Continuation of application No. 17/755,770, filed as application No. PCT/US2020/059198 on Nov. 5, 2020.

(60) Provisional application No. 62/931,466, filed on Nov. 6, 2019.

(51) Int. Cl.
| | |
|---|---|
| *A61K 31/196* | (2006.01) |
| *A61K 9/14* | (2006.01) |
| *A61K 31/165* | (2006.01) |
| *A61K 31/167* | (2006.01) |
| *A61K 31/192* | (2006.01) |
| *A61K 31/245* | (2006.01) |
| *A61K 31/405* | (2006.01) |
| *A61K 31/416* | (2006.01) |
| *A61K 31/60* | (2006.01) |
| *A61K 31/7034* | (2006.01) |
| *A61K 47/10* | (2017.01) |
| *A61K 47/12* | (2006.01) |
| *A61K 47/20* | (2006.01) |
| *A61K 47/38* | (2006.01) |
| *A61K 9/00* | (2006.01) |

(52) U.S. Cl.
CPC .......... *A61K 31/196* (2013.01); *A61K 9/0014* (2013.01); *A61K 31/165* (2013.01); *A61K 31/167* (2013.01); *A61K 31/192* (2013.01); *A61K 31/245* (2013.01); *A61K 31/405* (2013.01); *A61K 31/416* (2013.01); *A61K 31/60* (2013.01); *A61K 31/7034* (2013.01); *A61K 47/10* (2013.01); *A61K 47/12* (2013.01); *A61K 47/20* (2013.01); *A61K 47/38* (2013.01)

(58) Field of Classification Search
CPC .. A61K 31/196; A61K 9/0014; A61K 31/165; A61K 31/167; A61K 31/192; A61K 31/245; A61K 31/405; A61K 31/146; A61K 31/60; A61K 31/7034; A61K 47/10; A61K 47/12; A61K 47/20; A61K 47/38
See application file for complete search history.

(56) References Cited

U.S. PATENT DOCUMENTS

| | | | |
|---|---|---|---|
| 4,626,539 A | 12/1986 | Aungst et al. | |
| 4,885,174 A | 12/1989 | Bodor et al. | |
| 4,983,396 A | 1/1991 | Bodor et al. | |
| 7,622,138 B2 | 11/2009 | Murthy | |
| 8,980,290 B2 * | 3/2015 | Carrara | A61K 31/56 514/534 |
| 9,012,402 B1 | 4/2015 | Blanchard | |
| 9,101,591 B2 | 8/2015 | Kisak et al. | |
| 10,702,469 B2 | 7/2020 | Patel | |
| 2005/0020552 A1 | 1/2005 | Aschkenasy et al. | |
| 2008/0319092 A1* | 12/2008 | Singh | A61K 47/20 514/784 |
| 2010/0120918 A1* | 5/2010 | Patel | A61P 29/00 514/567 |
| 2011/0300083 A1 | 12/2011 | Yontz et al. | |
| 2012/0213842 A1 | 8/2012 | Birbara | |
| 2012/0244090 A1 | 9/2012 | Martinetti et al. | |
| 2014/0088195 A1* | 3/2014 | Buyuktimkin | A61P 25/06 514/570 |
| 2016/0022603 A1 | 1/2016 | Spakevicius et al. | |
| 2016/0101077 A1 | 4/2016 | Bannister et al. | |
| 2016/0213784 A1 | 7/2016 | Kisak et al. | |
| 2018/0250242 A1* | 9/2018 | Spakevicius | A61K 9/08 |
| 2019/0046438 A1 | 2/2019 | Hnat | |

FOREIGN PATENT DOCUMENTS

| | | |
|---|---|---|
| CA | 1280974 C | 3/1991 |
| CA | 2420895 A | 3/2002 |
| CN | 102652730 B | 4/2014 |
| DE | 4301783 C1 | 2/1994 |
| GR | 1004995 B | 9/2005 |
| JP | S63225312 A | 9/1988 |

(Continued)

OTHER PUBLICATIONS

Bartosova and Bajgar, Transdermal Drug Delivery In Vitro Using Diffusion Cells. Curr Med Chem. 2012;19 (27):4671-4677.

Kezic, Methods for measuring in-vivo percutaneous absorption in humans. Hum Exp Toxicol. Apr. 2008;27(4):289-295.

Mcpherson and Cimino, Topical NSAID Formulations. Pain Med. Dec. 2013;14 Suppl 1:S35-S39.

Osborne, Diethylene glycol monoethyl ether: an emerging solvent in topical dermatology products. J Cosmet Dermatol. Dec. 2011;10(4):324-329.

(Continued)

*Primary Examiner* — Jared Barsky

(74) *Attorney, Agent, or Firm* — Acuity Law Group, PC; Michael A. Whittaker

(57) ABSTRACT

A topical cyclooxygenase (COX) inhibitor formulation comprising an inhibitor of COX-1 and/or COX-2, one or more long chain monounsaturated fatty acids, long chain monounsaturated fatty alcohols, terpenes, or combinations thereof; and a solvent mixture comprising ethanol, propylene glycol, 2-(2-Ethoxyethoxy)ethanol, and optionally dimethylsulfoxide.

8 Claims, 14 Drawing Sheets

(56) References Cited

FOREIGN PATENT DOCUMENTS

| | | |
|---|---|---|
| JP | H04124134 A | 4/1992 |
| JP | 2006-265153 A | 10/2006 |
| JP | 2014-513132 A | 5/2014 |
| JP | 2015-164950 A | 9/2015 |
| JP | 2016-502530 A | 1/2016 |
| MX | 9800545 A | 4/1998 |
| MX | 9705070 A | 7/1998 |
| NZ | 222346 A | 8/1990 |
| NZ | 537359 A | 10/2006 |
| WO | 96030020 A1 | 10/1996 |
| WO | 98018417 A1 | 5/1998 |
| WO | 2004054552 A1 | 7/2004 |
| WO | 2005060540 A2 | 7/2005 |
| WO | 2009047785 A2 | 4/2009 |
| WO | 2009081217 A1 | 7/2009 |
| WO | 2013088375 A1 | 6/2013 |
| WO | 2014143964 A2 | 9/2014 |
| WO | 2016033308 A1 | 3/2016 |
| WO | 2017173269 A1 | 10/2017 |
| WO | 2018203040 A1 | 11/2018 |

OTHER PUBLICATIONS

International Search Report and Written Opinion issued in PCT/US2020/059198 dated Feb. 5, 2021 (10 pages).
Office Action issued by the JPO in Japanese Patent Application No. 2019-502529 dated Feb. 24, 2021—Engl transl only.
International Search Report and Written Opinion dated Jun. 22, 2017, for International Application No. PCT/US2017/025373, 6 pages.
Extended European Search Report issued in EP 17776775 dated Nov. 11, 2019 (7 pages).
DailyMed entry for PENNSAID 2% Topica, Feb. 8, 2022 (6 pages).
Exploratory Study of PENNSAID Gel to Treat Symptoms of Knee Osteoarthritis, ClinicalTrials.gov Identifier: NCT01119898, 2019 (10 pages).
PENNSAID Prescribing Information, 2022 (19 pages).

* cited by examiner

TOPICAL FORMULATIONS OF CYCLOOXYGENASE INHIBITORS AND THEIR USE

The present application is a continuation of U.S. patent application Ser. No. 17/755,770, which is the United States national phase application based on International Patent Application No. PCT/US20/59198, filed Nov. 5, 2020, which claims the benefit of U.S. Provisional Application No. 62/931,466, filed Nov. 6, 2019, each of which is hereby incorporated in its entirety including all tables, figures, and claims.

BACKGROUND OF THE DISCLOSURE

The following discussion of the background of the disclosure is merely provided to aid the reader in understanding the disclosure and is not admitted to describe or constitute prior art to the present disclosure.

Cyclooxygenase (COX, also known as prostaglandin-endoperoxide synthase), refers to a family of enzymes responsible for formation of prostanoids, including thromboxane and prostaglandins such as prostacyclin, from arachidonic acid. As the prostanoids are mediators of pain and inflammation, COX represents a common pharmaceutical target. Agents that inhibit prostaglandin G/H synthase (cyclooxygenase or COX), an enzyme that catalyzes the production of prostanoids, including prostaglandins, prostacyclin and thromboxane, from arachidonic acid, are referred to as COX inhibitors. Common nonsteroidal anti-inflammatory drugs (NSAIDs), such as aspirin and ibuprofen, exert their effects through inhibition of enzymes COX-1 and COX-2, while NSAIDS such ascelecoxib and etoricoxib are specific to the COX-2 isozyme. Acetaminophen, while not considered an NSAID because it has only minor anti-inflammatory activity, treats pain by blocking COX-2 while also inhibiting endocannabinoid reuptake.

The use of COX inhibitors in a topical formulation may be beneficial in reducing the likelihood of a patient experiencing adverse effects associated with systemic therapy. Medications applied directly to the skin may be either intended for local action or systemic effects. Topically applied medications (e.g., topical patches, creams, gels, ointments, solutions, etc.) may be intended to reach local tissue to achieve the desired therapeutic effect, or may act transdermally to result in systemic concentrations comparable with orally administered medications.

There are several topical NSAID products available in the United States approved to treat painful conditions. Diclofenac sodium 1% gel (Voltaren Gel) is approved for the relief of pain due to osteoarthritis in joints amenable to topical treatment, such as the knees and those of the hands. This product contains a variety of additional ingredients in the vehicle including isopropyl alcohol, propylene glycol, and water to assist in drug penetration of the skin. Diclofenac sodium topical solution 1.5% w/w (PENNSAID) is indicated for the treatment of signs and symptoms of osteoarthritis of the knee(s). Additional absorption-enhancing ingredients in this product include DMSO, propylene glycol, water and alcohol. A diclofenac epolamine 1.3% topical patch (Flector Patch) is indicated for the topical treatment of acute pain due to minor strains, sprains, and contusions. The patch is composed of an adhesive material containing 1.3% diclofenac epolamine, applied to a non-woven polyester felt backing and covered with a polypropylene film release liner which is removed prior to application.

Evidence indicates that topical formulations can achieve therapeutic concentrations of drug in localized tissue while maintaining low serum levels of drug and potentially avoiding systemic toxicity. Topical diclofenac preparations have a reported maximum serum concentration that is 0.4-2.2% of the maximum serum concentration achieved with oral diclofenac, resulting in significantly lower systemic exposure. High drug concentration at the site of action paired with low systemic concentrations can lead to efficacy greater than or equal to that of systemic NSAIDs with a reduced risk of adverse effects.

BRIEF SUMMARY OF THE DISCLOSURE

In a first aspect, the present disclosure provides topical cyclooxygenase (COX) inhibitor formulations. These formulations comprise:

an inhibitor of COX-1 and/or COX-2;
between about 1.0 and about 15.0 wt % of long chain monounsaturated fatty acids, long chain monounsaturated fatty alcohols, terpenes, or combinations thereof;
between 0 and about 5.0 wt % of a poloxamer;
between 0 and about 5.0 wt % of a pharmaceutically acceptable cellulosic excipient;
a solvent mixture comprising ethanol, propylene glycol, 2-(2-Ethoxyethoxy)ethanol, and optionally dimethylsulfoxide; and
wherein the formulation comprises about 5.0 wt % or less water.

In various embodiments, the formulation comprises one or more COX inhibitors selected from the group consisting of cannabinoids (e.g., tetrahydrocannabinol (D9-THC), tetrahydro-cannabinolic acid-A (THCA-A), cannabidiol (CBD), cannabidiolic acid (CBDA), cannabigerol (CBG) and cannabigerolic acid (CBGA)), Naproxen, Acetaminophen, Benzydamine, Bufexamac, Diclofenac, Etofenamate, Flufenamic acid, Ibuprofen, Indomethacin, Ketoprofen, and salicylates (e.g., salicylic acid, salicin, diflunisal, magnesium salicylate, choline salicylate). Preferably, the formulation comprises Diclofenac, and most preferably the formulation comprises between about 1.0 and about 2.5 wt % Diclofenac. In certain embodiments, the one or more COX inhibitors in the formulation comprise or consist of about 2 wt % diclofenac. The COX inhibitors may be present as a free acids or as various salts (e.g., diclofenac sodium, naproxen sodium, trolamine salicylate, ibuprofen lysine, etc.) or esters (e.g., diclofenac ethyl ester, naproxen methyl ester, methyl salicylate, ibuprofen diethylaminoethyl ester, etc.).

In certain embodiments, the formulation provides a percutaneous absorption of a COX inhibitor such as Diclofenac of at least 7% of the COX inhibitor present in the formulation. Percutaneous absorption (or skin permeation) can be visualized as consisting of a series of steps in sequence: sorption of a penetrant molecule onto the surface layers of stratum corneum, diffusion through it and the viable epidermis. At the papillary layer of the dermis, the molecule is taken up into the microcirculation for subsequent systemic distribution. Methods for measuring percutaneous absorption of topically applied drugs are known in the art. See, e.g., Kezic, Hum. Exp. Toxicol. 2008 27(4): 289-95. doi: 10.1177/0960327107085825. A topical COX inhibitor formulation according the present claims preferably provides a percutaneous absorption of the COX inhibitor of at least 10%.

In certain embodiments, the topical COX inhibitor formulation of the disclosure comprises no more than about 2.5 wt %, and preferably about 1 wt % or less, water. In most preferred embodiments, the formulation is anhydrous. By "anhydrous" is meant that the formulation does not include the use of water, either added as water per se or as a component of one of the liquid solvents. By way of example, 95% ethanol, which is an azeotrope comprising 5% water, is not used in an anhydrous formulation. Water which is a component of a hydrated ionic compound or that results from hygroscopic absorption, however, may be present in such an anhydrous formulation.

The term "wt %" as used herein refers to (mass of the component/total mass of the formulation)×100. By way of example, 2 wt % diclofenac is 2 g diclofenac per 100 g of the formulation.

The term "long chain monounsaturated fatty acid" refers to fatty acids having at least 14 carbons and a single double bond. The term "long chain monounsaturated fatty alcohol" refers to an equivalent alcohol (that is, an –OH group attaches to the terminal carbon rather than an alkoxy). For example, the formula for oleic acid is $CH_3(CH_2)_7CH{=}CH(CH_2)_7COOH$, while the formulation for the equivalent oleyl alcohol is $CH_3(CH_2)_7{-}CH{=}CH{-}(CH_2)_8OH$. Examples of monounsaturated fatty acids falling within this group include, but are not limited to, the following:

| | |
|---|---|
| Myristoleic acid | 14:1 (n-5) |
| Palmitoleic acid | 16:1 (n-7) |
| cis-Vaccenic acid | 18:1 (n-7) |
| Vaccenic acid | 18:1 (n-7) |
| Paullinic acid | 20:1 (n-7) |
| Oleic acid | 18:1 (n-9) |
| Elaidic acid (trans-oleic acid) | 18:1 (n-9) |
| 11-Eicosenoic acid (gondoic acid) | 20:1 (n-9) |
| Erucic acid | 22:1 (n-9) |
| Brassidic acid | 22:1 (n-9) |
| Nervonic acid | 24:1 (n-9) |
| Sapienic acid | 16:1 (n-10) |
| Gadoleic acid | 20:1 (n-11) |
| Petroselinic acid | 18:1 (n-12) |

In various embodiments, the long chain monounsaturated fatty acids and/or long chain monounsaturated fatty alcohols present in the formulation are C16:1 to C22:1 fatty acids or alcohols. In preferred embodiment, the long chain monounsaturated fatty acids present in the formulation comprise or consist of between about 1 and about 15 wt % oleic acid or oleyl alcohol or a mixture thereof, more preferably between about 1 and about 10 wt % oleic acid or oleyl alcohol or a mixture thereof, and most preferably between about 1 and about 5 wt % oleic acid or oleyl alcohol or a mixture thereof. In certain embodiments, the long chain monounsaturated fatty acids present in the formulation comprise or consist of about 1 wt % oleic acid or oleyl alcohol or a mixture thereof, about 2 wt % oleic acid or oleyl alcohol or a mixture thereof, about 3 wt % oleic acid or oleyl alcohol or a mixture thereof, about 4 wt % oleic acid or oleyl alcohol or a mixture thereof, about 5 wt % oleic acid or oleyl alcohol or a mixture thereof, about 6 wt % oleic acid or oleyl alcohol or a mixture thereof, about 7 wt % oleic acid or oleyl alcohol or a mixture thereof, about 8 wt % oleic acid or oleyl alcohol or a mixture thereof, about 9 wt % oleic acid or oleyl alcohol or a mixture thereof, or about 10 wt % oleic acid or oleyl alcohol or a mixture thereof.

Poloxamers are nonionic triblock copolymers composed of a central hydrophobic chain of polyoxypropylene flanked by two hydrophilic chains of polyoxyethylene. these copolymers are commonly named with the letter P (for poloxamer) followed by three digits: the first two digits multiplied by 100 give the approximate molecular mass of the polyoxypropylene core, and the last digit multiplied by 10 gives the percentage polyoxyethylene content. Examples of poloxamers which may find use in the present disclosure include, but are not limited to, poloxamer –101, –105, –105 benzoate, –108, –122, –123, –124, –181, –182, –182 dibenzoate, –183, –184, –185, –188, –212, –215, –217, –231, –234, –235, –237, –238, –282, –284, –288, –331, –333, –334, –335, –338, –401, –402, –403, and –407. In preferred embodiment, the poloxamer present in the formulation comprises, or consists of, between about 0.1 and about 5 wt % poloxamer–188 or contains no poloxamer.

Cellulose and its derivatives (e.g., ether and ester derivatives) are among the excipients frequently used in pharmaceutical compounded and industrialized products with various purposes. Among their uses are as suspending agents in oral liquid preparations and as viscosity increasing agents in topical formulations. Examples of pharmaceutically acceptable cellulosic excipients which can find use in the disclosure include, but are not limited to, hydroxypropylcellulose, hydroxypropyl methylcellulose, carboxymethylcellulose, methylcellulose, ethylcellulose, hydroxyethyl cellulose, hydroxyethylmethylcellulose and ethyl hydroxyethylcellulose. In preferred embodiment, the pharmaceutically acceptable cellulosic excipients present in the formulation comprises, or consists of, between about 1.0 and about 5 wt % of hydroxypropylcellulose. In certain embodiments, the cellulosic excipients in the formulation comprise or consist of about 1 wt % of hydroxypropylcellulose, about 2 wt % of hydroxypropylcellulose, about 3 wt % of hydroxypropylcellulose, about 4 wt % of hydroxypropylcellulose, or about 5 wt % of hydroxypropylcellulose. In certain other embodiments, the formulation is free of cellulosic excipients.

An exemplary topical COX inhibitor formulation according to the present disclosure comprises a solvent mixture as follows:

between about 25.0 and about 50.0 wt % ethanol, between about 2.0 and about 12.5 wt % propylene glycol, between about 0 and about 25.0 wt % dimethylsulfoxide, and between about 20.0 and about 49.9 wt % 2-(2-Ethoxyethoxy)ethanol; and wherein the solvent mixture is between about 70.0 and about 95.0 wt % of the formulation, and wherein the formulation has about 1 wt % or less water and is preferably anhydrous.

In certain embodiments, the formulation comprises between about 7.5 and about 12.5 wt % propylene glycol, and more preferably between about 10 and about 12 propylene glycol wt % propylene glycol.

In certain embodiments, the formulation comprises between about 10 and about 30 wt % 2-(2-Ethoxyethoxy)ethanol, and more preferably between about 20 and about 27.5 wt % 2-(2-Ethoxyethoxy)ethanol.

In certain embodiments, the formulation comprises between about 25 and about 45 wt % ethanol, and more preferably between about 30 and about 40 wt % ethanol.

In certain embodiments, the formulation comprises between about 15 and about 25 wt % dimethylsulfoxide, and more preferably between about 20 wt % dimethylsulfoxide. In certain other embodiments, the formulation comprises less than 15 wt % dimethylsulfoxide, preferably less than 10 wt % dimethylsulfoxide, more preferably less than 5 wt % dimethylsulfoxide, and still more preferably 0 wt % dimethylsulfoxide.

A preferred topical COX inhibitor formulation comprises or consists of:
between about 1.0 and about 2.5 wt % diclofenac;
between about 1.0 and about 10.0 wt % of a long chain monounsaturated fatty acid, a long chain monounsaturated alcohol, or mixtures thereof;
between 0 and about 5.0 wt % of a poloxamer;
between about 2.0 and about 5.0 wt % of a pharmaceutically acceptable cellulosic excipient;
an anhydrous solvent mixture comprising ethanol, propylene glycol, dimethylsulfoxide, and 2-(2-Ethoxyethoxy)ethanol,
wherein the formulation comprises between about 25.0 and about 40.0 wt % ethanol, between about 2.0 and about 12.5 wt % propylene glycol, between about 15.0 and about 25.0 wt % dimethylsulfoxide, and between about 20.0 and about 49.9 wt % 2-(2-Ethoxyethoxy)ethanol; and wherein the solvent mixture is between about 70.0 and about 95.0 wt % of the formulation, and wherein the formulation has about 1 wt % or less water and is preferably anhydrous.

A preferred topical COX inhibitor formulation according to the disclosure is anhydrous and comprises or consists of:
about 2 wt % Diclofenac;
about 27% ethanol;
about 8 wt % oleic acid, oleyl alcohol, or a mixture thereof;
about 0.5% poloxamer 188;
about 11% propylene glycol;
about 3 wt % hydroxypropylcellulose;
about 21% wt % dimethylsulfoxide; and
about 25 wt % 2-(2-Ethoxyethoxy)ethanol.

Another preferred topical COX inhibitor formulation according to the disclosure is anhydrous and comprises or consists of:
about 2.0 wt % Diclofenac;
about 43.5% ethanol;
about 4.0 wt % oleic acid, oleyl alcohol, or a mixture thereof;
0 wt % poloxamer 188;
about 3.0 wt % propylene glycol;
about 3.0 wt % hydroxypropylcellulose;
about 20.0 wt % dimethylsulfoxide; and
about 24.5 wt % 2-(2-Ethoxyethoxy)ethanol.

Another preferred topical COX inhibitor formulation according to the disclosure is anhydrous and comprises or consists of:
about 2.0 wt % Diclofenac;
about 37.5% ethanol;
about 2.0 wt % oleic acid, oleyl alcohol, or a mixture thereof;
0 wt % poloxamer 188;
about 11.0 wt % propylene glycol;
about 3.0 wt % hydroxypropylcellulose;
about 20.0 wt % dimethylsulfoxide; and
about 24.5 wt % 2-(2-Ethoxyethoxy)ethanol.

The term "about" as used throughout the specification with regard to a value refers to +/−10% of the given value.

A list of exemplary formulations of the disclosure may be found in the following tables. In each case, the values recited in the tables can include +/−10% of each value within their scope:

| Ingredient | Wt % | Wt % | Wt % | Wt % | Wt % |
|---|---|---|---|---|---|
| Oleic Acid | 8.0 | 8.0 | 8.0 | 8.0 | 8.0 |
| DMSO | 45.5 | 45.5 | 45.5 | 25.5 | 0 |
| Transcutol | 26.5 | 27.0 | 0 | 20.0 | 45.5 |
| Sodium Diclofenac | 2.0 | 1.5 | 2.0 | 2.0 | 2.0 |
| Propylene Glycol | 11.0 | 11.0 | 11.0 | 11.0 | 11.0 |
| Poloxamer P188 | 3.0 | 3.0 | 3.0 | 3.0 | 3.0 |
| 100% Ethyl Alcohol | 0 | 0 | 26.5 | 26.5 | 27 |
| Hydroxypropyl Cellulose | 4.0 | 4.0 | 4.0 | 4.0 | 4.0 |
| Water | 0 | 0 | 0 | 0 | 0 |
| TOTAL | 100 | 100 | 100 | 100 | 100 |

| Ingredient | Wt % | Wt % | Wt % | Wt % |
|---|---|---|---|---|
| Oleic Acid | 8.0 | 8.0 | 8.0 | 4.0 |
| DMSO | 21.0 | 21.0 | 21.0 | 20.0 |
| Transcutol | 26.0 | 26.0 | 26.0 | 24.5 |
| Sodium Diclofenac | 2.0 | 2.0 | 2.0 | 2.0 |
| Propylene Glycol | 11.0 | 11.0 | 11.0 | 3.0 |
| Poloxamer P188 | 3.0 | 0.5 | 0 | 0 |
| 100% Ethyl Alcohol | 26.0 | 28.5 | 29.0 | 43.5 |
| Hydroxypropyl Cellulose | 3.0 | 3.0 | 3.0 | 3.0 |
| Water | 0 | 0 | 0 | 0 |
| TOTAL | 100 | 100 | 100 | 100 |

| Ingredient | Wt % | Wt % | Wt % | Wt % | Wt % |
|---|---|---|---|---|---|
| Oleic Acid | 8.0 | 8.0 | 8.0 | 4.0 | 2.0 |
| DMSO | 20.0 | 20.0 | 20.0 | 20.0 | 20.0 |
| Transcutol | 24.5 | 24.5 | 24.5 | 24.5 | 24.5 |
| Sodium Diclofenac | 2.0 | 2.0 | 2.0 | 2.0 | 2.0 |
| Propylene Glycol | 11.0 | 6.0 | 3.0 | 11.0 | 11.0 |
| Poloxamer P188 | 0 | 0 | 0 | 0 | 0 |
| Ethyl Alcohol | 31.5 | 36.5 | 39.5 | 35.5 | 37.5 |
| Hydroxypropyl Cellulose | 3.0 | 3.0 | 3.0 | 3.0 | 3.0 |
| Water | 0 | 0 | 0 | 0 | 0 |
| TOTAL | 100 | 100 | 100 | 100 | 100 |

| Ingredient | Wt % | Wt % | Wt % | Wt % |
|---|---|---|---|---|
| Oleic Acid | 8.0 | 8.0 | 8.0 | 8.0 |
| DMSO | 16.0 | 21.0 | 16.0 | 21.0 |
| Transcutol | 26.0 | 21.0 | 21.0 | 16.0 |
| Sodium Diclofenac | 2.0 | 2.0 | 2.0 | 2.0 |
| Propylene Glycol | 11.0 | 11.0 | 11.0 | 11.0 |
| Poloxamer P188 | 0 | 0 | 0 | 0 |
| Ethyl Alcohol | 34.0 | 34.0 | 39.0 | 39.0 |
| Hydroxypropyl Cellulose | 3.0 | 3.0 | 3.0 | 3.0 |
| Water | 0 | 0 | 0 | 0 |
| TOTAL | 100 | 100 | 100 | 100 |

| Ingredient | Wt % |
|---|---|
| Oleic Acid | 0 |
| Glycerin | 0 |
| DMSO | 20.0 |
| Transcutol | 24.5 |
| Sodium Diclofenac | 2.0 |

-continued

| Ingredient | Wt % |
|---|---|
| Propylene Glycol | 11.0 |
| Poloxamer P188 | 0 |
| Ethyl Alcohol Dehydrated | 35.5 |
| Hydroxypropyl Cellulose | 3.0 |
| Water | 0 |
| Oleyl Alcohol | 4.0 |
| TOTAL | 100 |

In a related aspect, the present disclosure provides methods for topically treating a pain episode at a location on the human body, comprising topically applying a topical COX inhibitor formulation according to the disclosure to the location. In various embodiments the pain episode is an acute pain episode or a chronic pain episode. Examples of pain episodes which may be treated include, but are not limited to, pain resulting from osteoarthritis, rheumatoid arthritis, mild-to-moderate inflammation and tissue injury, low back pain, inflammatory arthropathies (e.g., ankylosing spondylitis, psoriatic arthritis, reactive arthritis), tennis elbow, headache, postoperative pain, muscle stiffness and pain due to Parkinson's disease, and traumatic injury. In preferred embodiments, the present methods are for topically treating pain of osteoarthritis of the knee(s), comprising topically applying a topical COX inhibitor formulation according to the disclosure to the knee(s).

In certain embodiments, the dose of a topical COX inhibitor formulation according to the disclosure applied provides a COX inhibitor amount of about 80 mg, about 40 mg, about 30 mg, about 20 mg, or about 10 mg. In certain embodiments, for example, application of 4 mL of a 2 wt % diclofenac formulation will provide a topical dose of 80 mg of diclofenac; 2 mL will provide 40 mg of diclofenac, 1 mL will provide 20 mg of diclofenac, etc.

In some embodiments, a formulation of the disclosure is in the form of a gel, lotion, cream, spray, aerosol, ointment, emulsion, suspension, liposomal system, lacquer, patch, bandage, buccal tablet, wafer, sublingual tablet, suppository, vaginal dosage form or occlusive dressing. In a particular embodiment, the formulation is a gel. In some embodiments, a formulation of the present disclosure is applied directly to the skin as, for example, a gel, an ointment, or a cream or indirectly through a patch, bandage, or other occlusive dressing. A formulation of the disclosure may be applied once daily, or multiple times per day depending upon the condition of the patient. In some embodiments, said formulation is adapted for a once, twice, three times or four times daily administration for as long as desired, suitably on the order of days to weeks to months, or longer if desired. The compositions can be administered to any skin surface, including the hand, arms, trunk, back, legs, feet, etc.

It is to be understood that the disclosure is not limited in its application to the details of construction and to the arrangements of the components set forth in the following description or illustrated in the drawings. The disclosure is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

DETAILED DESCRIPTION OF THE DISCLOSURE

Figure 1:
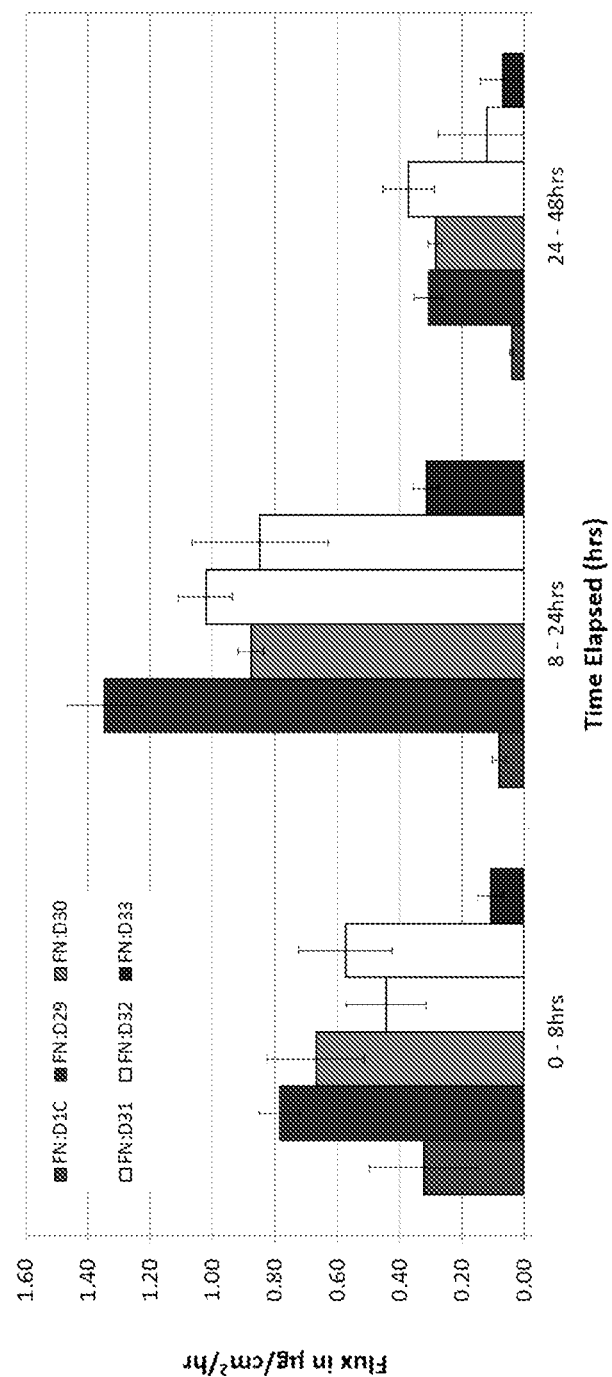
FIG. 1: skin permeation flux data for 2% diclofenac formulations from Table 1.

The greatest hindrances in the topical, percutaneous delivery of COX inhibitors is the obstructive property of the stratum corneum (SC), the outermost layer of the skin, skin binding, skin metabolism, cutaneous toxicity and prolonged lag times.

Different methodologies have been developed to enhance transdermal absorption, including the use of drug derivatives, super-saturated systems, physical approaches, and chemical penetration enhancers (sorption promoters) that facilitate the diffusion of drugs through the SC. In that regard, numerous chemicals have been used for their skin permeation promoting capacity, including fatty acids, fatty acid esters, fatty alcohols or fatty alcohol ethers, fatty ethers, lower alcohols, glycerol esters, polyhydric alcohols, diols, amides (e.g., N,N-diethyl-m-toluamide), amines, terpenes, polar solvents, pyrrolidones and derivatives thereof, sulfoxides, azone or laurocapram, surface active agents, lecithin, polyols, glycols, quaternary ammonium compounds, silicones, alkanoates, certain biologies, enzymes, complexing agents, macrocyclics, solvents, etc.

As used herein, "permeation enhancement" refers to increasing the permeability of the skin to an active pharmaceutical ingredient (API), so as to increase the rate at which the API permeates through the skin. Similarly, "permeation enhancer" (PE) refers to an agent or mixture of agents that achieve such permeation enhancement. A PE mixture suitable for the instant disclosure promotes penetration of an API through the skin by one or more of the following mechanisms: (1) by increasing the diffusivity of the drug in the skin; (2) by causing SC lipid-fluidization, which leads to decreased barrier function (a reversible action); (3) by increasing and optimizing the thermodynamic activity of the drug in the vehicle; (4) by affecting the partition coefficient of the drug; and (5) by increasing its release from the formulation into the upper layers of the skin.

In certain embodiments, a PE mixture suitable for the instant disclosure has one or more of the following characteristics: non-toxic, non-irritant, non-allergenic, and/or non-sensitizing to skin; pharmacologically inert, at least at the concentrations required to exert adequate permeation action; immediate, predictive, and/or reversible effect; easily incorporated into pharmaceutical preparations; and cosmetically acceptable.

Fatty acid permeation enhancers

The PE mixture of the present disclosure preferably comprises one or more fatty acids such as a long chain fatty acids For example, the fatty acid may be oleic acid (cis-9-octadecenoic acid), or a functional derivative thereof. In certain embodiments, the PE is a fatty acid ester, fatty alcohol or fatty alcohol ether, fatty ether, lower alcohol, glycerol ester, polyhydric alcohol, diol, amide (e.g., N,N-diethyl-m-toluamide), amine, terpene, polar solvent or a mixture thereof. In certain embodiments, the fatty acid is alkanoic acid, capric acid, diacid, ethyloctadecanoic acid, hexanoic acid, lactic acid, lauric acid, linoelaidic acid, linoleic acid, linolenic acid, neodecanoic acid, oleic acid (cis-9-octadecenoic acid), palmitic acid, pelargonic acid, propionic acid, or vaccenic acid. In certain embodiments, the PE is at least one of a C8-C22 fatty acid, such as isopropyl myristate.

While not wishing to be bound by any particular theory, the fatty acid PEs of the disclosure are believed to selectively perturb the intercellular lipid bilayers in the SC, thus enhancing the penetration of the SC by the API. In certain embodiments, differences in penetration enhancing effects may be adjusted by adjusting the number of double bonds and cis/trans configuration of the fatty acid isomers, based on the general trend that unsaturated fatty acids are more effective (e.g., more than 5-fold, 10-fold, 15-fold, 20-fold or more) in enhancing percutaneous absorption than their saturated counterparts, especially for lipophilic drugs/APIs.

In certain embodiments, the PE is oleic acid, linoleic acid, a-linolenic acid, arachidonic acid, palmitic acid, lauric acid, caprylic acid, iso stearic acid, isopropyl myristate, or myristic acid, optionally further comprising one or more of propylene glycol, ethanol, 2-ethyl- 1,3-hexanediol, and dexpanthene. In certain embodiments, the PE is palmitic acid, and the topical formulation is formulated to enhance the penetration of an API to the SC (a particularly alkyl-rich region). In certain embodiments, the PE is myristic acid, and the topical formulation is formulated to enhance the penetration of an API to the epidermis. In certain embodiments, the PE is octyl salicylate, and the topical formulation is formulated to enhance the penetration of a water-soluble or oil-soluble API into the epidermis and dermis.

Additional fatty acid-based PEs can be found in MX 9705070, GR 1004995, US 2005-020552A1, WO 05/060540, CA 2,420,895, MX 9800545, WO 04/054552, NZ 537359, WO 98/18417, WO 96/30020, DE 4301783, US 4,885,174, US 4,983,396, NZ 222346, CA 1,280,974, and US 4,626,539.

Terpene permeation enhancers

Due to their high enhancement effect and low skin irritation, terpenes can find use in pharmaceutical and cosmetic formulations as permeation enhancers. Terpenes, primarily extracted from medicinal plants, are volatile compounds with molecular components that are composed of only carbon, hydrogen and oxygen atoms. The basic chemical structure of terpenes consists of a number of repeated isoprene (C5H8) units which are used to classify terpenes. A few terpenes (e.g., 1,8-cineole, menthol, and menthone) are included in the list of Generally Recognized As Safe (GRAS) agents issued by the U.S. Food and Drug Administration. Examples of terpenes suitable for the present disclosure may be selected from the group consisting of menthol, D-limonene, geraniol, nerolidol, and a mixture thereof.

Sulfoxide permeation enhancers

In certain embodiments, a PE mixture suitable for the instant disclosure comprises dimethylsulfoxide (DMSO), for enhancing the penetration of both hydrophilic and lipophilic APIs. Additional DMSO like PEs which may substitute for DMSO include similar, chemically related compounds such as Dimethylacetamide (DMAC), dimethylformamide (DMF), cyclic sulfoxides, decylmethyl sulfoxide, Dimethyl sulfoxide, and 2-Hydroxyundecyl methyl sulfoxide.

Glycol permeation enhancers

In certain embodiments, a PE mixture suitable for the instant disclosure comprises one or more glycol-based compounds such as a monoalkyl ether of diethylene glycol, preferably diethylene glycol monoethyl ether or diethylene glycol monomethyl ether or other dipropylene glycol, propylene glycol, 1,2-butylene glycol, etc. Currently, the Inactive Ingredients Database of the U.S. Food and Drug Administration (FDA) lists diethylene glycol monoethyl ether (Transcutol) for topical (up to 49.9%) and transdermal (up to 5%) routes of administration. An important property of Transcutol is its capacity to dissolve a broad range of hydrophilic and lipophilic actives. Its ability to outperform PG and EtOH in solubilization power makes it a highly useful pharmaceutical excipient. With a negative log P of ~0.5, Transcutol is considered as a polar protic solubilizer that demonstrates affinity and good miscibility with also hydrophobic groups. The ability of solvents having a negative log P to readily penetrate the stratum corneum contrasts with lipophilic actives (log P values of 2-3) more readily penetrating the stratum corneum than actives having negative log P values. Transcutol is compatible with most pharmaceutical excipients; soluble in common solvents like glycerin, ethanol, propylene glycol, and water; miscible with polar lipids like medium-chain triglycerides and polyethylene glycol based surfactants (polyoxylglycerides); but insoluble in non-polar mineral oil or dimethicone. Owing to its high solubility and miscibility with water, Transcutol may hydrate depending on the relative humidity conditions.

Emulsifying agents

Producing a formulation for topical application to skin or mucosal surface can often require mixing an oil phase with an emulsifying agent. An emulsifying agent is a pharmaceutically acceptable surfactant, which may be a small molecule, oligomer or polymer. It may be nonionic, cationic or anionic. It may be of natural or synthetic origin.

Numerous emulsifying agents may be used in the instant disclosure. In certain embodiments, the emulsifying agent may comprise: sodium lauryl sulfate, or a non-ionic emulsifier (such as glyceryl stearate and/or PEG 100 stearate). Other representative emulsifiers include, but are not limited to, gelatin, casein, lecithin (phosphatides), gum acacia, cholesterol, tragacanth, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens, polyoxyethylene stearates, colloidal silicon dioxide, sodium dodecylsulfate, carboxymethylcellulose calcium, carboxymethylcellulose sodium, methylcellulose, hydroxyethylcellulose, hydroxypropylcellulose, microcrystalline cellulose, and magnesium aluminum silicate. Most of these surface modifiers are known pharmaceutical excipients and are described in detail in the Handbook of Pharmaceutical Excipients, published jointly by the American Pharmaceutical Association and The Pharmaceutical Society of Great Britain, the Pharmaceutical Press, 1986.

Other examples of surfactants include tyloxapol, poloxamers and polyxamines. Poloxamers are water-soluble triblock copolymers composed of hydrophilic polyethylene oxide (PEO) and hydrophobic polypropylene oxide (PPO) blocks linked together. The amphiphilic nature of these block copolymers can be varied by controlling the length of the PEO and/or PPO block components (Ahmed et al., 2001). Several members of this poloxamer family of chemicals (such as poloxamer 188 and 407) are known to be biocompatible and non-toxic to mammalian cells and tissues, making them useful for biomedical applications. These surfactants are known to incorporate into or onto mammalian cell membranes, and thereby reduce protein adsorption and cell adhesion.

Still other emulsifiers include lecithin, dialkylesters of sodium sulfo succinic acid, such as Aerosol OT, which is a dioctyl ester of sodium sulfo succinic acid, available from American Cyanamid, Duponol P, which issodium lauryl sulfate, available from DuPont, Triton X-200, which is an alkyl aryl polyether sulfonate, available from Rohm and Haas, Tween ® 20 and Tween® 80, which are polyoxyethylene sorbitan fatty acid esters, available from Croda, Inc.; Crodesta F-1 10, which is a mixture of sucrose stearate and sucrose distearate, available from Croda, Inc., Crodesta SL-40, which is available from Croda, Inc., and SA90HCO, which is Ci8H37-CH2(CON(CH3)CH2(CHOH)4CH$_2$OH) 2, decanoyl-N-methylglucamide; n-decyl-P-D-glucsopyranoside; n-decyl-P-D-maltopyranoside; n-dodecyl-P-D-glucopyranoside; n-dodecyl-P-D-maltoside; heptanoyl-N-methylglucamide; n-heptyl-P-D-glucopyranoside; n-heptyl-P-D-thioglucoside; n-hexyl-P-D-glucopyranoside; nonanoyl-N-methylglucamide; n-noyl-P-D-glucopyranoside; octanoyl-N-methylglucamide; n-octyl-P-D-glucopyranoside; octyl-P-D-thioglucopyranoside; and the like.

Many polymeric emulsifiers such as poloxamers and cellulosic excipients also act as gelling agents. Gels are semi-solid, three dimensional, polymeric matrices comprising small amounts of solid dispersed in relatively large amount of liquid, yet possessing more solid like character. Gels exhibit mechanical properties characteristic of the solid state, both the dispersed component and the dispersion medium extend themselves continuously throughout the whole system. Gels are often transparent or translucent semisolid formulations which are favored by patients due to their unobtrusiveness. Topical gel formulation provides a suitable delivery system for drugs because they are less greasy and provide better application property and stability in comparison to cream and ointments.

Other ingredients

In certain embodiments, the compositions may further comprise one or more additives or combinations thereof, including but not limited to: wetting agents; texture enhancers; humidity regulators; pH regulators; osmotic pressure modifiers; UV-A and UV-B screening agents; and antioxidants. For example, antioxidants can be a-tocopherol, butylated hydroxyanisole or butylated hydroxytoluene, superoxide dismutase, ubiquinol, or certain metal-chelating agents. One skilled in this art will be able to select the optional compound(s) to be added to these compositions such that the advantageous properties intrinsically associated with the present disclosure are not, or are not substantially, adversely affected by the envisaged addition.

In addition, the compositions may further comprise one or more one or more additional active agents such as an antihistamine; a corticosteroid, a local anesthetic agent, a topical analgesic and an antibiotic. In various embodiments, the antihistamine may be diphenhydramine hydrochloride or chlorpheniramine maleate; the corticosteroid may be hydrocortisone, a hydrocortisone-21-monoester, (such as hydrocortisone-21-acetates, hydrocortisone-21-butyrate, hydrocortisone-21-propionate, hydrocortisone-21-valerate, etc., and a hydrocortisone-17,21-diester, (such as hydrocortisone-17,21-diacetate, hydrocortisone-17-acetate-21-butyrate, hydrocortisone-17,21-dibutyrate), dexamethasone, flumethasone, prednisolone, methylprednisolone, clobetasol propionate, betamethasone benzoate, betamethasone dipropionate, diflorasone diacetate, fluocinonide, mometasone furoate, or triamcinolone acetonide; the local anesthetic agent may be benzocaine, lidocaine, prilocaine and dibucaine; and the topical analgesic may be 1-menthol, d,1-camphor or capsaicin.

Preferred embodiments of the disclosure:
1. A topical cyclooxygenase (COX) inhibitor formulation, comprising
    one or more COX inhibitors that inhibit human COX-1, human COX-2, or both human COX-1 and human COX-2;
    between about 1.0 and about 15.0 wt % of long chain monounsaturated fatty acids, long chain monounsaturated fatty alcohols, terpenes, or combinations thereof;
    between 0 and about 5.0 wt % of a poloxamer;
    between about 1.0 and about 5.0 wt % of a pharmaceutically acceptable cellulosic excipient;
    a solvent mixture comprising ethanol, propylene glycol, 2-(2-Ethoxyethoxy)ethanol, and optionally dimethylsulfoxide; and
    wherein the formulation comprises about 5.0 wt % or less water.
2. A topical COX inhibitor formulation according to embodiment 1, wherein the formulation comprises a COX inhibitor selected from the group consisting of Naproxen, Acetaminophen, Benzydamine, Bufexamac, Diclofenac, Etofenamate, Flufenamic acid, Ibuprofen, Indomethacin, Ketoprofen, salicylic acid, salicin, diflunisal, magnesium salicylate, and choline salicylate.
3. A topical COX inhibitor formulation according to embodiment 2, wherein the COX inhibitor present in the formulation comprises or consists of Diclofenac.
4. A topical COX inhibitor formulation according to embodiment 3, wherein the formulation comprises between about 1.0 and about 2.5 wt % Diclofenac.
5. A topical COX inhibitor formulation according to embodiment 4, wherein the formulation provides a percutaneous absorption of the Diclofenac of at least about 7%.
6. A topical COX inhibitor formulation according to embodiment 5, wherein the formulation provides a percutaneous absorption of the Diclofenac of at least about 10%.

7. A topical COX inhibitor formulation according to one of embodiments 1-6, wherein the formulation comprises about 1.0 wt % or less water.

8. A topical COX inhibitor formulation according to embodiment 7, wherein the formulation is anhydrous.

9. A topical COX inhibitor formulation according to one of embodiments 1-8, wherein the formulation comprises between about 25.0 and about 50.0 wt % ethanol, between about 2.0 and about 12.5 wt % propylene glycol, between about 0 and about 25.0 wt % dimethylsulfoxide, and between about 20.0 and about 49.9 wt % 2-(2-Ethoxyethoxy)ethanol; and wherein the solvent mixture is between about 70.0 and about 95.0 wt % of the formulation.

10. A topical COX inhibitor formulation according to one of embodiments 1-9, wherein the formulation comprises between about 1.0 and about 10.0 wt % of a long chain monounsaturated fatty acid, a long chain monounsaturated alcohol, or mixtures thereof.

11. A topical COX inhibitor formulation according to one of embodiments 1-10, wherein the long chain monounsaturated fatty acid, a long chain monounsaturated alcohol, or mixtures thereof present in the formulation comprises or consists of oleic acid, oleyl alcohol, or a mixture thereof.

12. A topical COX inhibitor formulation according to one of embodiments 1-11, wherein the formulation comprises a poloxamer selected from the group consisting of poloxamer-101, -105, -105 benzoate, -108, -122, -123, -124, -181, -182, -182 dibenzoate, -183, -184, -185, -188, -212, -215, -217, -231, -234, -235, -237, -238, -282, -284, -288, -331, -333, -334, -335, -338, -401, -402, -403, and -407.

13. A topical COX inhibitor formulation according to embodiment 12, wherein the formulation comprises between 0 and about 5.0 wt % of poloxamer-188.

14. A topical COX inhibitor formulation according to one of embodiments 1-11, wherein the formulation comprises a pharmaceutically acceptable cellulosic excipient selected from the group consisting of hydroxypropylcellulose, hydroxypropyl methylcellulose, carboxymethylcellulose, methylcellulose, ethylcellulose, hydroxyethyl cellulose, hydroxyethylmethylcellulose and ethyl hydroxyethylcellulose.

15. A topical COX inhibitor formulation according to embodiment 14, wherein the formulation comprises between about 1.0 and about 5.0 wt % of hydroxypropylcellulose.

16. A topical COX inhibitor formulation according to embodiment 1, wherein the formulation comprises:
between about 1.0 and about 2.5 wt % diclofenac;
between about 1.0 and about 10.0 wt % of long chain monounsaturated fatty acids, long chain monounsaturated fatty alcohols, or mixtures thereof, and preferably the long chain monounsaturated fatty acids, long chain monounsaturated fatty alcohols, or mixtures thereof comprise or consist of oleic acid, oleyl alcohol, or a mixture thereof;
between 0 and about 5.0 wt % of a poloxamer;
between about 2.0 and about 5.0 wt % of a pharmaceutically acceptable cellulosic excipient and preferably the pharmaceutically acceptable cellulosic excipient comprises or consists of hydroxypropylcellulose;
an anhydrous solvent mixture comprising ethanol, propylene glycol, dimethylsulfoxide, and 2-(2-Ethoxyethoxy)ethanol,
wherein the formulation comprises between about 25.0 and about 50.0 wt % ethanol, between about 2.0 and about 12.5 wt % propylene glycol, between about 15.0 and about 25.0 wt % dimethylsulfoxide, and between about 20.0 and about 49.9wt % 2-(2-Ethoxyethoxy)ethanol; and wherein the solvent mixture is between about 70.0 and about 95.0 wt % of the formulation.

17. A topical COX inhibitor formulation according to embodiment 1, wherein the formulation is anhydrous and comprises or consists of:
about 2.0 wt % Diclofenac;
about 27.0 wt % ethanol;
about 8.0 wt % oleic acid, oleyl alcohol, or a mixture thereof;
about 0.5 wt % poloxamer 188;
about 11.0 wt % propylene glycol;
about 3.0 wt % hydroxypropylcellulose;
about 21.0 wt % dimethylsulfoxide; and
about 25.0 wt % 2-(2-Ethoxyethoxy)ethanol.

18. A topical COX inhibitor formulation according to embodiment 1, wherein the formulation is anhydrous and comprises or consists of:
about 2.0 wt % Diclofenac;
about 43.5% ethanol;
about 4.0 wt % oleic acid, oleyl alcohol, or a mixture thereof;
0 wt % poloxamer 188;
about 3.0 wt % propylene glycol;
about 3.0 wt % hydroxypropylcellulose;
about 20.0 wt % dimethylsulfoxide; and
about 24.5 wt % 2-(2-Ethoxyethoxy)ethanol.

19. A topical COX inhibitor formulation according to embodiment 1, wherein the formulation is anhydrous and comprises or consists of:
about 2.0 wt % Diclofenac;
about 37.5% ethanol;
about 2.0 wt % oleic acid, oleyl alcohol, or a mixture thereof;
0 wt % poloxamer 188;
about 11.0 wt % propylene glycol;
about 3.0 wt % hydroxypropylcellulose;
about 20.0 wt % dimethylsulfoxide; and
about 24.5 wt % 2-(2-Ethoxyethoxy)ethanol.

20. A topical COX inhibitor formulation according to embodiment 1, wherein the formulation is anhydrous and comprises or consists of:
about 2.0 wt % Diclofenac;
about 31.5% ethanol;
about 8.0 wt % oleic acid, oleyl alcohol, or a mixture thereof;
0 wt % poloxamer 188;
about 11.0 wt % propylene glycol;
about 3.0 wt % hydroxypropylcellulose;
about 20.0 wt % dimethylsulfoxide; and
about 24.5 wt % 2-(2-Ethoxyethoxy)ethanol.

21. A method of topically treating a pain episode at a location on the human body, comprising topically applying a topical COX inhibitor formulation according to one of embodiments 1-20 to the location.

22. A method according to embodiment 21, wherein the pain episode is an acute pain episode.

23. A method according to embodiment 21, wherein the pain episode is a chronic pain episode.

24. A method of topically treating pain of osteoarthritis of the knee(s), comprising topically applying a topical COX inhibitor formulation according to one of embodiments 1-20 to the knee(s).

25. A method according to one of embodiments 21-24, wherein the COX inhibitor is diclofenac, and the topical dose of diclofenac is about 80 mg or less.
26. A method according to embodiment 25, wherein the topical dose of diclofenac is about 80 mg, about 40 mg, about 30 mg, about 20 mg, or about 10 mg.
27. A method according to one of embodiments 21-26, wherein the topical COX inhibitor formulation comprises about 2 wt % diclofenac.

EXAMPLES

The following examples serve to illustrate the present disclosure. These examples are in no way intended to limit the scope of the disclosure.

Example 1: Topical Diclofenac formulations

Materials:
DMSO, CAS Number: 67-68-5
Oleic acid , CAS Number 112-80-1
Trascutol (Diethylene glycol monoethyl ether; 2-(2-Ethoxyethoxy)ethanol), CAS Number 111-90-0
Ethyl alcohol, 200 proof, anhydrous, CAS Number 64-17-5
Poloxamer 188, CAS Number 9003-11-6
1,2-Propanediol (propylene glycol), CAS Number: 57-55-6
Klucel™ GF Pharm (hydroxypropyl cellulose (HPC), CAS number: 9004-64-2)
Sodium Diclofenac (2-[(2,6-Dichlorophenyl)amino]benzeneacetic acid sodium salt), CAS Number: 15307-79-6
Procedure for Making 2% Diclofenac formulation:
Heat oleic acid to 60° C, then mix and dissolve Poloxamer 188 in the oleic acid.
At 20° C add propylene glycol to DMSO while mixing. Slowly add the hydroxypropyl cellulose to the mixture. Mix for 1 hour.
Heat transcutol to 60° and dissolve sodium diclofenac in the transcutol.
While mixing, add transcutol/sodium diclofenac to DMSO/propylene glycol. Combine with oleic acid/Poloxamer 188, then add ethanol and mix until homogeneous.
Alternative procedure without Poloxamer 188:
At 20° C add propylene glycol to DMSO while mixing.
At 20° C dissolve sodium diclofenac in transcutol.
While mixing, add transcutol/sodium diclofenac to DMSO/propylene glycol. Slowly add the hydroxypropyl cellulose to the mixture. Then add ethanol and mix until homogeneous. Add oleic acid and mix until homogeneous.
Exemplary formulation of the present disclosure (wt %)
Sodium Diclofenac 1.8-2.2 wt %
DMSO 18.0-22.0 wt %
Transcutol 15.0-25.0%
Propylene glycol 10.0-12.0 wt %
Ethyl Alcohol 25.0-40.0 wt %
Hydroxypropyl cellulose 2.7-3.3 wt %
Poloxamer P188 0.0-3.0 wt %
Oleic acid 7.0-9.0 wt %

Example 2. Permeation Testing

Franz diffusion cell experiments were used to analyze flux rates of diclofenac from compositions taught under the present disclosure across human skin. See, e.g., Bartosova and Bajgar, Transdermal Drug Delivery In Vitro Using Diffusion Cells, Curr. Med. Chem. 2012, 19: 4671-4677.
In the examples described herein, Franz diffusion cells ("FDC"s) with a 3.3 mL receptor well volume were used, with either porcine skin or human cadaver skin. For human cadaver skin, split thickness human cadaver skin (0.015"-0.018") was obtained from AlloSource (Centennial, Colo.) or Skin Bank New York Firefighters (New York, N.Y.). The skin tissue was dermatomed by the tissue bank to a thickness of some 250 μm and shipped frozen on dry ice. All information available from the cadaver skin supplier pertaining to the source of the tissue, donor information, the part of the body, the condition of the tissue, and the duration of storage prior to receipt were maintained in study files. Upon receipt of the donor skin, the skin pieces were stored at −20° C. until used. Prior to use, the skin pieces were removed from the freezer and allowed to thaw fully at ambient temperature.

The donor well addresses a skin area of about 0.55 cm$^2$. The receptor wells were filled with PBS containing 0.01% sodium azide (the "Receptor Fluid"), this fluid having been verified as providing sink conditions throughout the experiments. The receptor wells of the FDCs were maintained at 37° C. (the temperature on the surface of the skin is 32(±0.5)° C.) in a stirring dry block with continual agitation of the Receptor Fluid in the receptor well using a magnetic stir bar. Donor and receptor chambers were clamped about the skin piece under uniform pressure using a pinch clamp.

After the FDCs were assembled, the skin was allowed to hydrate for 20 minutes in contact with the receptor fluid. Any FDCs that evidenced any leakage during this period were discarded.

The integrity and quality of each skin piece was tested prior to application of the test formulations through measurement of the transdermal flux of tritiated water or of the transepidermal electrical resistance ("TEER") (skin integrity was usually not tested on porcine skin pieces). The TEER measurements were performed as follows. An aliquot of 150 μL of PBS was introduced into each FDC donor well. After 10 minutes, a blunt electrode probe was placed into the donor well to rests lightly on the surface of the skin under its own weight. A second electrode was then inserted into receptor fluid via the sample port on the receptor chamber of the FDC. An alternating current ("AC") signal, 100 mV root mean square ("RMS") at 100 Hz, was applied across the skin using a waveform generator and the impedance is then measured with a digital multimeter and the results recorded in kΩ. Any FDC showing anomalously low impedance (nominally <2 kΩ) was discarded and the FDCs were ranked according to the magnitudes of the measured impedance readings. Test articles were then assigned to the batch of FDCs such that the replicates for each test article are each applied to a skin piece with nearly equivalent average transepidermal electrical resistance values.

After the membrane integrity tests were complete and the cells appropriately sorted, samples of the test articles were then applied to the stratum corneum of the skin. A one-time dosing regimen was used for the studies. Six replicates of each of the test formulations are examined, typically in a batch of some 36 FDCs in total.

Doses were applied using a Nichiryo positive displacement pipettor. The doses were dispensed from the pipettor to the skin and spread across the surface using the blunt end of a glass rod. The typical aspirated dose was 10 mL of the formulation per cell for most experiments. The formulations themselves were typically made at 1 wt %. Assuming a 10 mL dose applied to the skin, no loss to the glass rod when spreading the formulation, 1 wt % of the active in the formulation, a specific gravity of 1.0 for the formulation and a surface area of 0.55 cm² per cell, then each FDCs was dosed at ~181.8 mg/cm² of diclofenac.

A sample was abstracted from each receptor well at preset times, typically 24 h. Using a graduated Hamilton type injector syringe, a 300 µl aliquot was abstracted from the sampling port of each FDC at 24 hours. Each abstracted aliquot was introduced into a well in a 96-well microtiter plate. Samples were stored in a refrigerator at 4-8° C. prior to HPLC analysis. Samples were analyzed within 5 days of collection.

At 24 hours, the skin was then tape stripped three times with cellophane tape, each tape stripping consisting of applying a piece of cellophane tape to the skin with light pressure and peeling off the tape, thereby systematically removing the upper most layers of the stratum corneum. The tape strips were discarded.

After tape tripping was complete, the remaining skin was split into epidermal and dermal compartments by using a pair of spatulas. If necessary, the skin was placed on a hot plate set at 60° C. for one minute to help facilitate the separation of the skin. The epidermal and dermal compartments were then separately placed into glass vials, into which 3 mL of DMSO was added. The skin pieces were then incubated at 40° C. for 24 hours with gentle agitation. After the 24 hour incubation period, samples were collected.

The samples abstracted from receptor wells and skin extractions were then analyzed by the verified HPLC method using Chemstation software. The AUCs of the diclofenac were recorded and converted to mg/ml values using a calibration curve developed from the calibration standards' AUC values and known concentration values. These mg/ml values were imported into the study results Excel workbook. These concentrations were then multiplied by the receptor volume (3.3 mL), or skin extraction volume (3 ml) and divided by the surface area of the skin exposed to the receptor fluid (0.55 cm2) for an end cumulative amount in mg/cm2. The concentrations of the Active were assayed and reported in each case.

Formulations tested (Table 1)

Figure 2:
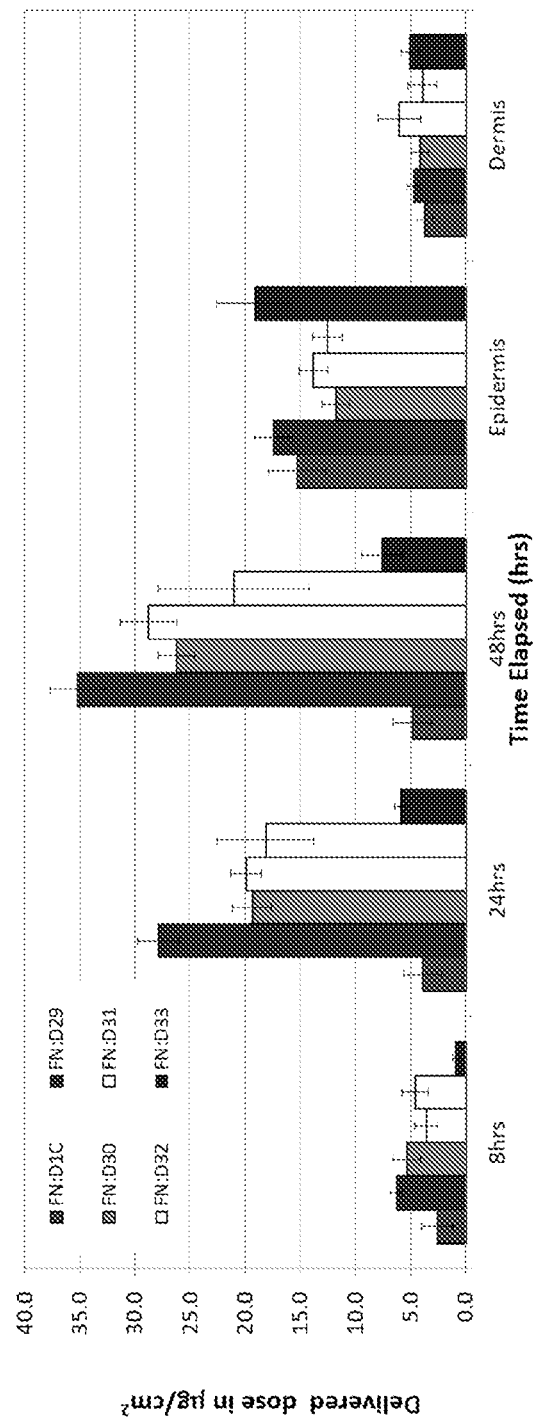
FIG. 2: skin permeation delivered dose data for 2% diclofenac formulations from Table 1.

FIG. 1 depicts skin permeation flux data for 2% diclofenac formulations from Table 1, while FIG. 2 depicts skin permeation delivered dose data for 2% diclofenac formulations from Table 1.

Example 3

Extrapolating from formulation D32, additional formulations which contained reduced amounts of DMSO and increased amounts of transcutol were examined by the same procedure.

Formulations tested (Table 2):

| Ingredient | Formula D1C PENNSAID 2% Diclofenac Wt % | Formula D34 Wt % | Formula D35 Wt % | Formula D36 Wt % |
| --- | --- | --- | --- | --- |
| Oleic Acid | 0 | 8.0 | 8.0 | 8.0 |
| DMSO | 45.5 | 21.0 | 21.0 | 21.0 |
| Transcutol | 0 | 26.0 | 26.0 | 26.0 |
| Sodium Diclofenac | 2.0 | 2.0 | 2.0 | 2.0 |
| Propylene Glycol | 11.0 | 11.0 | 11.0 | 11.0 |
| Poloxamer P188 | 0 | 3.0 | 0.5 | 0 |
| 100% Ethyl Alcohol | 31.35 | 26.0 | 28.5 | 29.0 |
| Hydroxypropyl Cellulose | 3.0 | 3.0 | 3.0 | 3.0 |
| Water | 7.15 | 0 | 0 | 0 |
| TOTAL | 100 | 100 | 100 | 100 |

Figure 3:
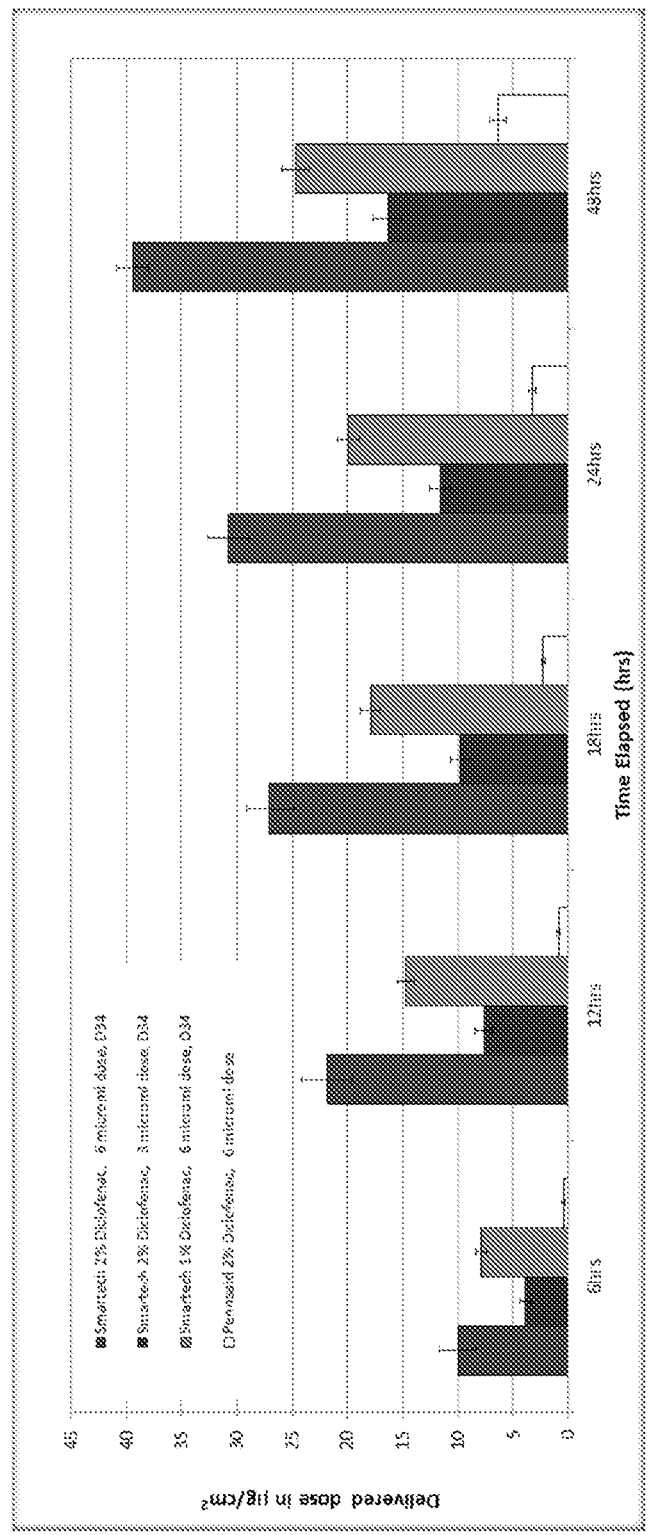
FIG. 3: delivered transdermal dose data for 2% diclofenac formulations D34 and Pennsaid.
Figure 4:
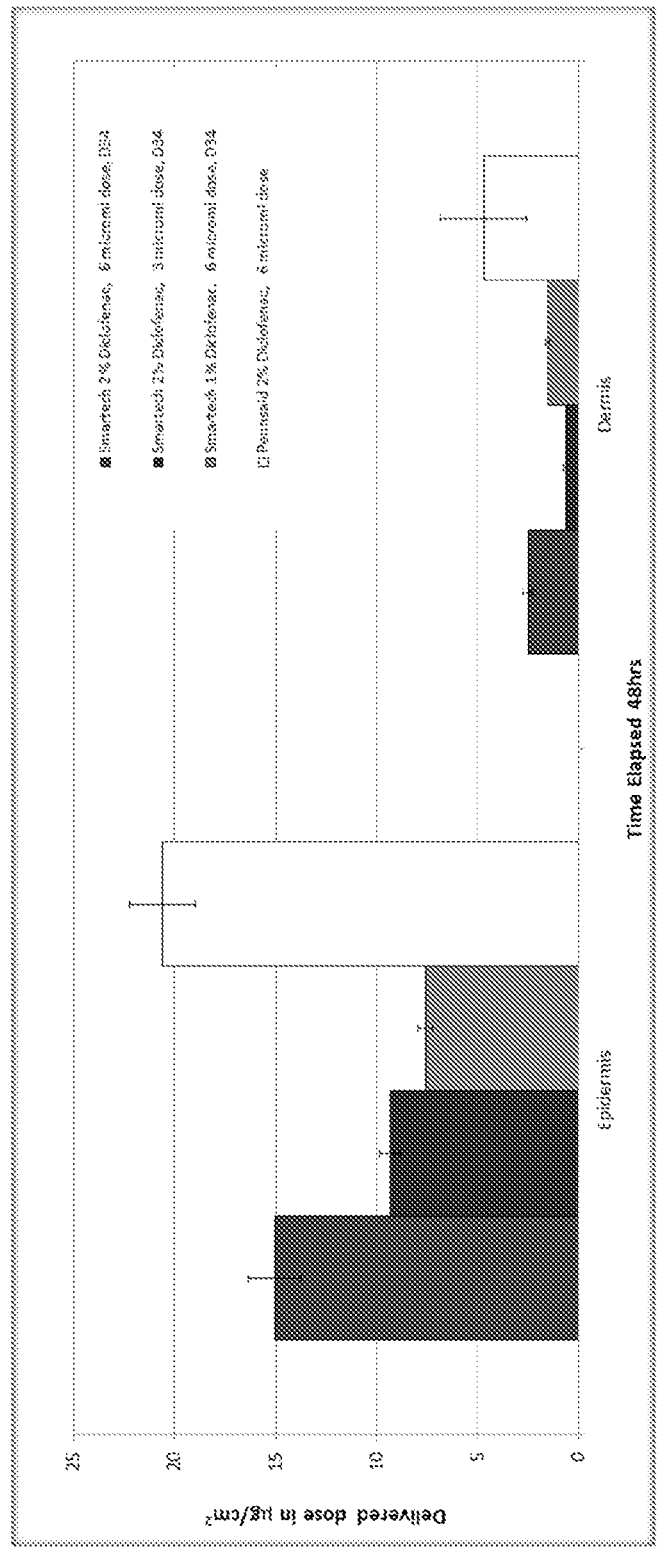
FIG. 4: skin retained dose data for 2% diclofenac formulations D34 and Pennsaid.
Figure 5:
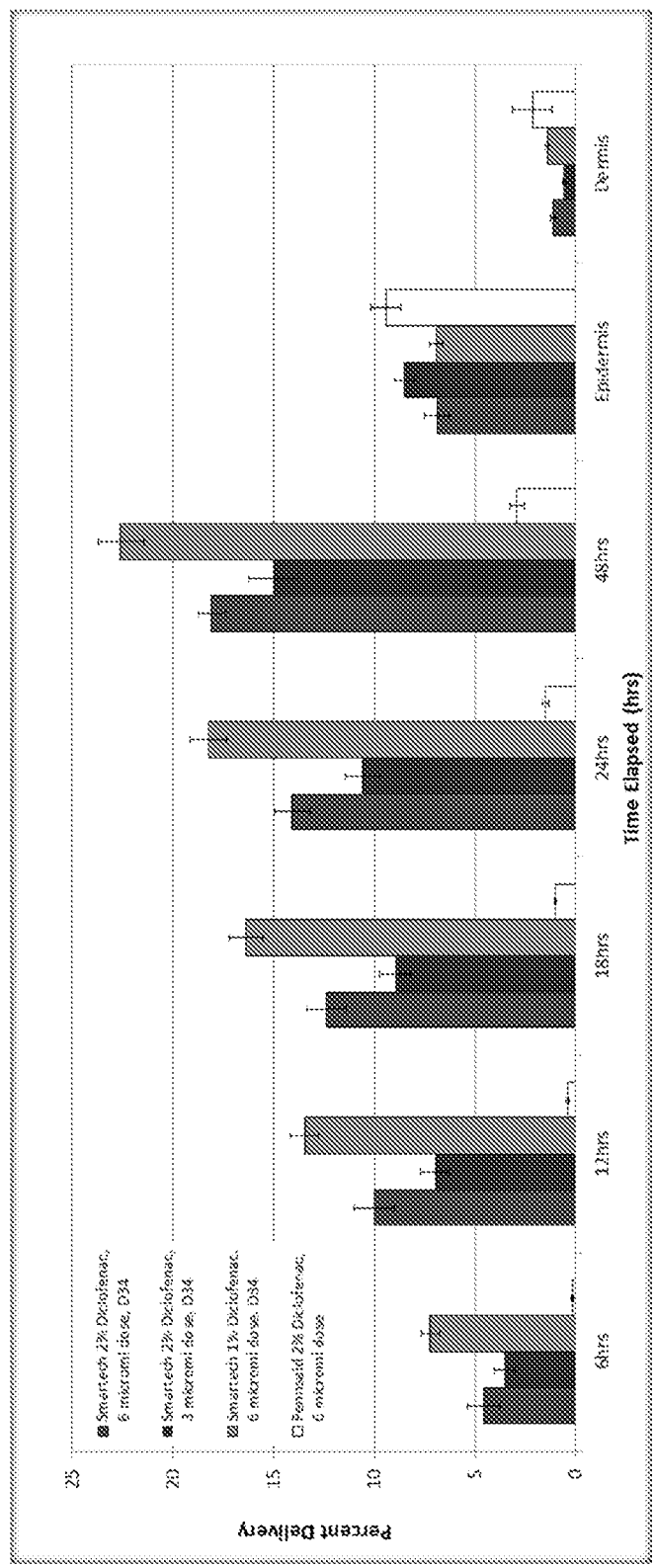
FIG. 5: delivered transdermal dose data for 2% diclofenac formulations D34 and Pennsaid as a percent delivery of diclofenac.

FIGS. 3, 4 and 5 depict a head-to-head comparison of Pennsaid and Formulation D34 as a delivered transdermal dose, dose retained in the skin, and calculated as percent delivery of diclofenac. As can be seen, formulation D34 delivered significantly more diclofenac transdermally than did Pennsaid, while Pennsaid exhibited a greater amount retained in the epidermis and dermis. The percent transdermal delivery of diclofenac from formulation D34 was greater than 15% at 48 hours.

Figure 6:
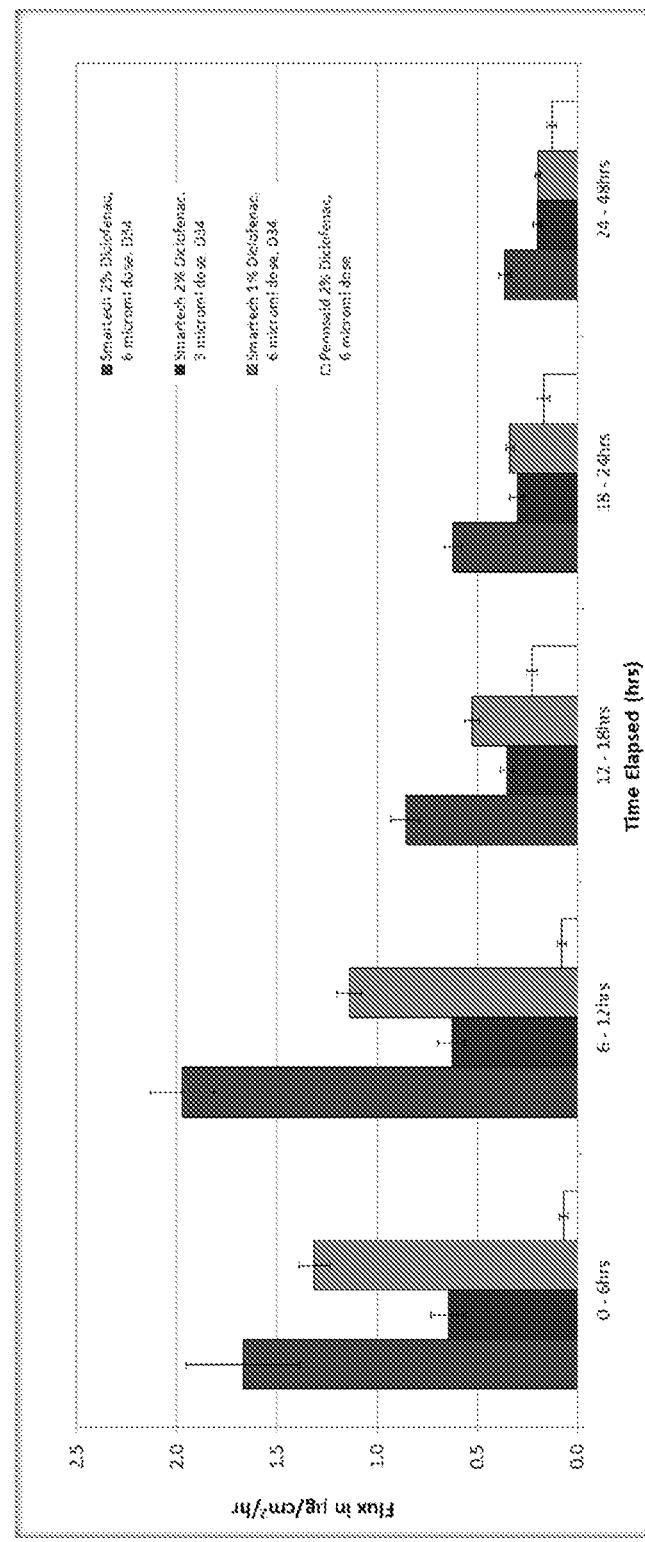
FIG. 6: skin permeation flux data for 2% diclofenac formulations D34 and Pennsaid.

FIG. 6 shows the diclofenac flux over time for these two formulations. A maximum diclofenac flux was observed within 12 hours of application.

| Ingredient | Formula D1C (PENNSAID 2%) Wt % | Formula D29 Wt % | Formula D30 Wt % | Formula D31 Wt % | Formula D32 Wt % | Formula D33 Wt % |
| --- | --- | --- | --- | --- | --- | --- |
| Oleic Acid | 0 | 8.0 | 8.0 | 8.0 | 8.0 | 8.0 |
| DMSO | 45.5 | 45.5 | 45.5 | 45.5 | 25.5 | 0 |
| Transcutol | 0 | 26.5 | 27.0 | 0 | 20.0 | 45.5 |
| Sodium Diclofenac | 2.0 | 2.0 | 1.5 | 2.0 | 2.0 | 2.0 |
| Propylene Glycol | 11.0 | 11.0 | 11.0 | 11.0 | 11.0 | 11.0 |
| Poloxamer P188 | 0 | 3.0 | 3.0 | 3.0 | 3.0 | 3.0 |
| 100% Ethyl Alcohol | 31.35 | 0 | 0 | 26.5 | 26.5 | 27 |
| Hydroxypropyl Cellulose | 3.0 | 4.0 | 4.0 | 4.0 | 4.0 | 4.0 |
| Water | 7.15 | 0 | 0 | 0 | 0 | 0 |
| TOTAL | 100 | 100 | 100 | 100 | 100 | 100 |

Example 4

Additional formulations which vary the amounts of oleic acid, propylene glycol, and ethyl alcohol were examined by the same procedure.

Formulations tested (Table 3):

| Ingredient | Formula D1C PENNSAID 2% Diclofenac Wt % | Formula D51 Wt % | Formula D52 Wt % | Formula D53 Wt % | Formula D54 Wt % | Formula D55 Wt % |
|---|---|---|---|---|---|---|
| Oleic Acid | 0 | 8.0 | 8.0 | 8.0 | 4.0 | 4.0 |
| DMSO | 45.5 | 20.0 | 20.0 | 20.0 | 20.0 | 20.0 |
| Transcutol | 0 | 24.5 | 24.5 | 24.5 | 24.5 | 24.5 |
| Sodium Diclofenac | 2.0 | 2.0 | 2.0 | 2.0 | 2.0 | 2.0 |
| Propylene Glycol | 11.0 | 11.0 | 6.0 | 3.0 | 11.0 | 3.0 |
| Poloxamer P188 | 0 | 0 | 0 | 0 | 0 | 0 |
| Ethyl Alcohol | 31.35 | 31.5 | 36.5 | 39.5 | 35.5 | 43.5 |
| Hydroxypropyl Cellulose | 3.0 | 3.0 | 3.0 | 3.0 | 3.0 | 3.0 |
| Water | 7.15 | 0 | 0 | 0 | 0 | 0 |
| TOTAL | 100 | 100 | 100 | 100 | 100 | 100 |

Figure 7:
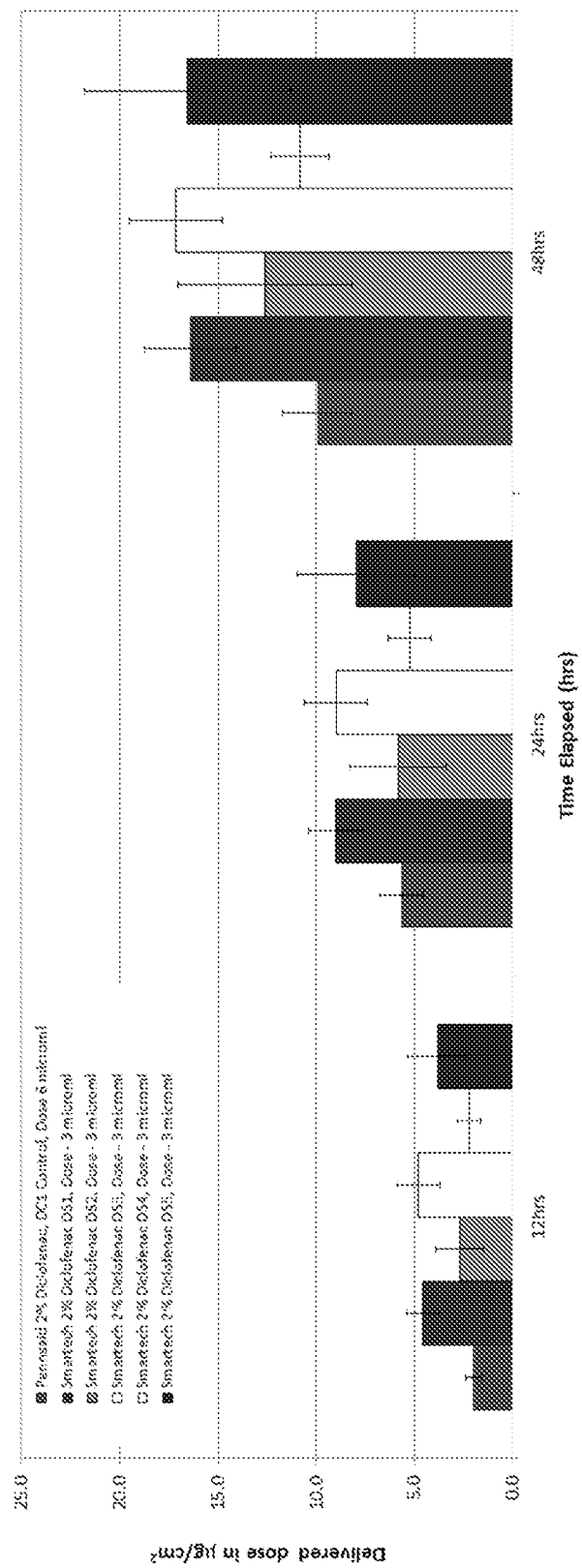
FIG. 7: delivered transdermal dose data for 2% diclofenac formulations D51-D55 and Pennsaid.
Figure 8:
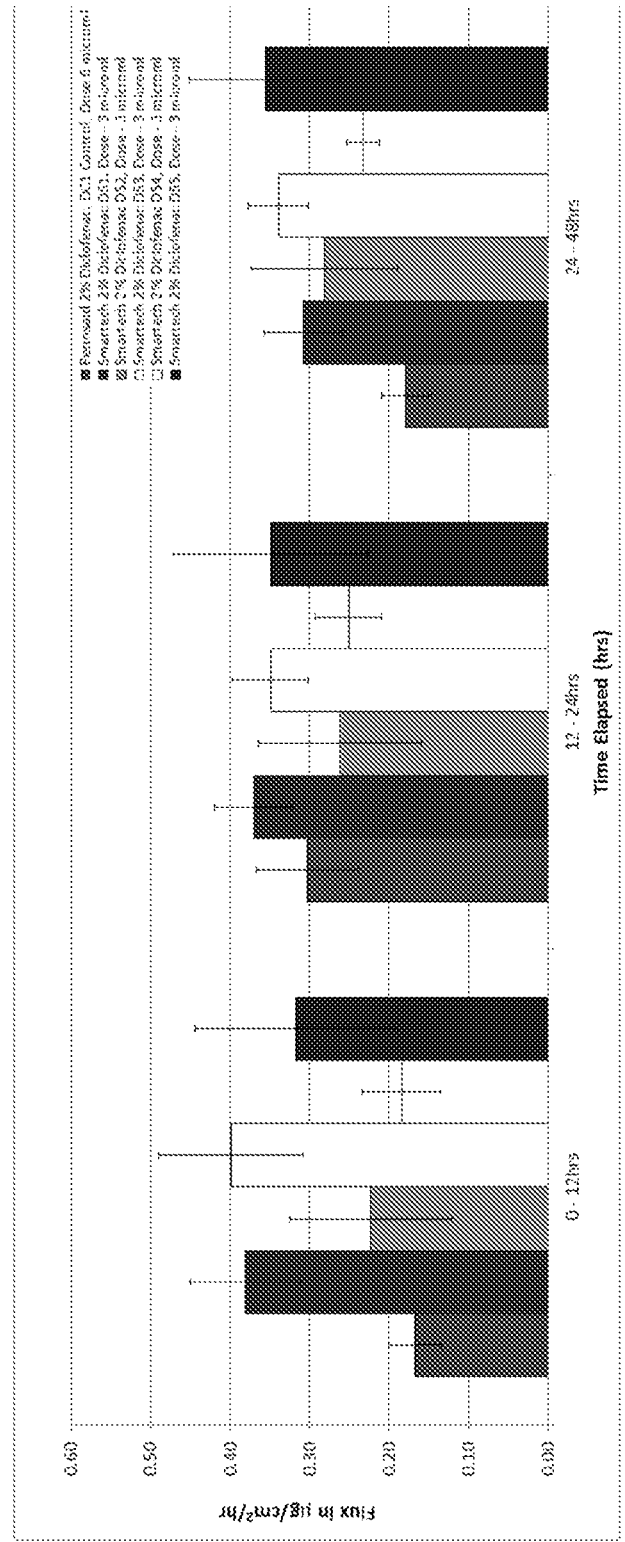
FIG. 8: skin permeation flux data for 2% diclofenac formulations formulations D51-D55 and Pennsaid.

FIG. 7 depicts skin permeation delivered dose data for 2% diclofenac formulations from Table 1, while FIG. 8 depicts skin permeation flux data for 2% diclofenac formulations from Table 1. As shown, these formulae can deliver equivalent amounts of diclofenac to that of Formula D1C with substantially less DMSO and at a much lower amount of the formula applied.

Example 5

Additional formulations which vary the amounts of transcutol and ethyl alcohol were examined by the same procedure.

Formulations tested (Table 4):

| Ingredient | Formula D1C PENNSAID 2% Diclofenac Wt % | Formula D37 Wt % | Formula D38 Wt % | Formula D39 Wt % | Formula D40 Wt % |
|---|---|---|---|---|---|
| Oleic Acid | 0 | 8.0 | 8.0 | 8.0 | 8.0 |
| DMSO | 45.5 | 16.0 | 21.0 | 16.0 | 21.0 |
| Transcutol | 0 | 26.0 | 21.0 | 21.0 | 16.0 |
| Sodium Diclofenac | 2.0 | 2.0 | 2.0 | 2.0 | 2.0 |
| Propylene Glycol | 11.0 | 11.0 | 11.0 | 11.0 | 11.0 |
| Poloxamer P188 | 0 | 0 | 0 | 0 | 0 |
| Ethyl Alcohol | 31.35 | 34.0 | 34.0 | 39.0 | 39.0 |
| Hydroxypropyl Cellulose | 3.0 | 3.0 | 3.0 | 3.0 | 3.0 |
| Water | 7.15 | 0 | 0 | 0 | 0 |
| TOTAL | 100 | 100 | 100 | 100 | 100 |

Figure 9:
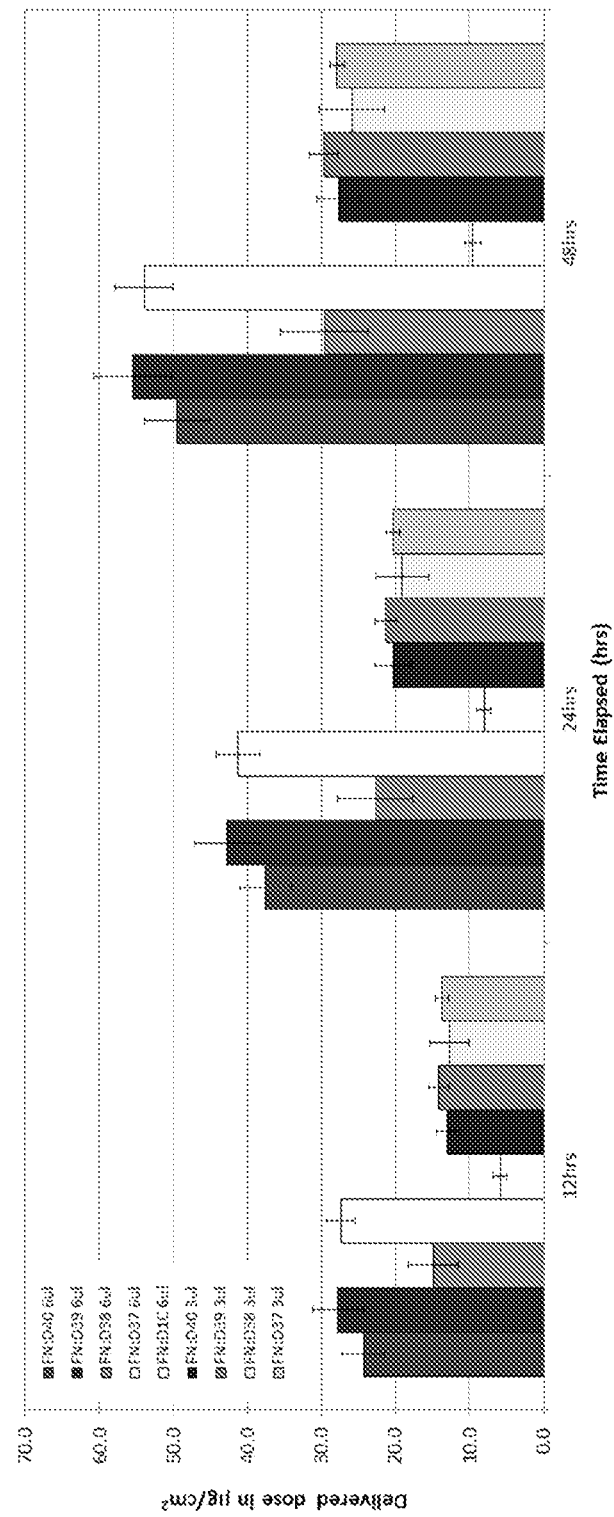
FIG. 9: delivered transdermal dose data for 2% diclofenac formulations D37-D39 and Pennsaid.
Figure 10:
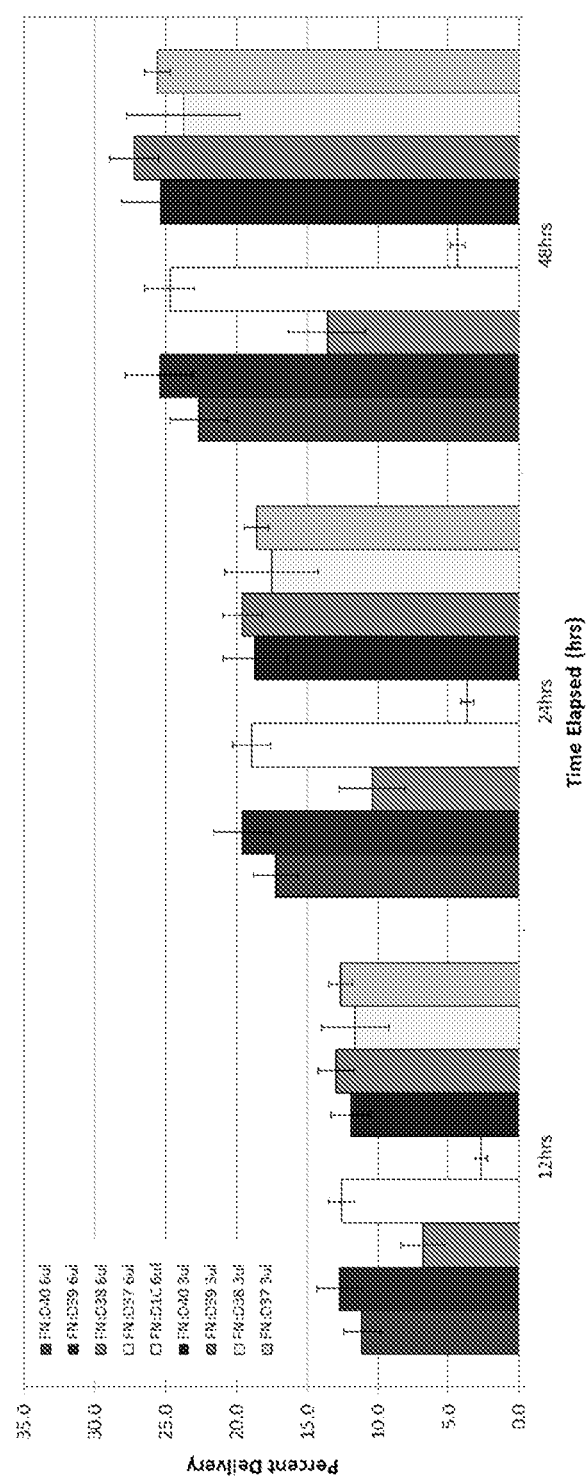
FIG. 10: delivered transdermal dose data for 2% diclofenac formulations D37-D39 and Pennsaid as a percent delivery of diclofenac.
Figure 11:
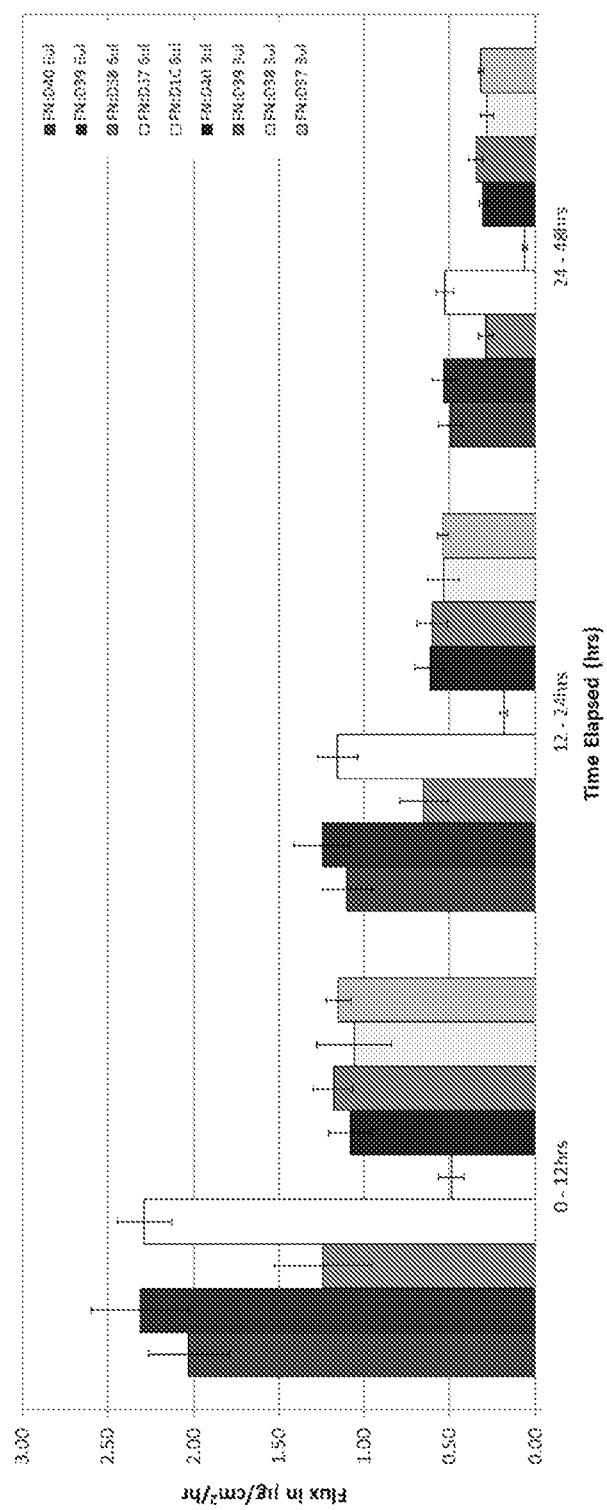
FIG. 11: skin permeation flux data for 2% diclofenac formulations formulations D37-D39 and Pennsaid.

FIGS. 9, 10, and 11 depict a head-to-head comparison of Pennsaid and Formulation D34 as a delivered transdermal dose, dose retained in the skin, and calculated as percent delivery of diclofenac.

Example 6

Additional formulations which vary the amounts of oleic acid, propylene glycol, and ethyl alcohol were examined by the same procedure.

Formulations tested (Table 5):

| Ingredient | Formula D1C PENNSAID 2% Diclofenac Wt % | Formula D51 Wt % | Formula D52 Wt % | Formula D53 Wt % | Formula D54 Wt % | Formula D55 Wt % | Formula D56 Wt % |
|---|---|---|---|---|---|---|---|
| Oleic Acid, | 0 | 8.0 | 8.0 | 8.0 | 4.0 | 4.0 | 2.0 |
| DMSO | 45.5 | 20.0 | 20.0 | 20.0 | 20.0 | 20.0 | 20.0 |
| Transcutol | 0 | 24.5 | 24.5 | 24.5 | 24.5 | 24.5 | 24.5 |
| Sodium Diclofenac | 2.0 | 2.0 | 2.0 | 2.0 | 2.0 | 2.0 | 2.0 |
| Propylene Glycol | 11.0 | 11.0 | 6.0 | 3.0 | 11.0 | 3.0 | 11.0 |
| Ethyl Alcohol (Dehydrated) | 31.35 | 31.5 | 36.5 | 39.5 | 35.5 | 43.5 | 37.5 |

-continued

| Ingredient | Formula D1C PENNSAID 2% Diclofenac Wt % | Formula D51 Wt % | Formula D52 Wt % | Formula D53 Wt % | Formula D54 Wt % | Formula D55 Wt % | Formula D56 Wt % |
|---|---|---|---|---|---|---|---|
| Hydroxypropyl Cellulose | 3.0 | 3.0 | 3.0 | 3.0 | 3.0 | 3.0 | 3.0 |
| Water | 7.15 | 0 | 0 | 0 | 0 | 0 | 0 |
| TOTAL | 100 | 100 | 100 | 100 | 100 | 100 | 100 |

In this group of formulations, the Oleic Acid concentration varied from a high concentration of 8.0% down to 2.0%. The test data started varying the dosage from 6 μL for Pennsaid and 3 μL for the formulations. This is the data that shows better penetration with the formulation at ½ the dose. In the second data set for formulation D56 a second dose of 6 μL of Pennsaid and 3 μL for Formulation D56 was used to simulate the application of a second application. The control for all data sets was the actual Pennsaid product. See FIGS. 12 and 13.

Figure 12:
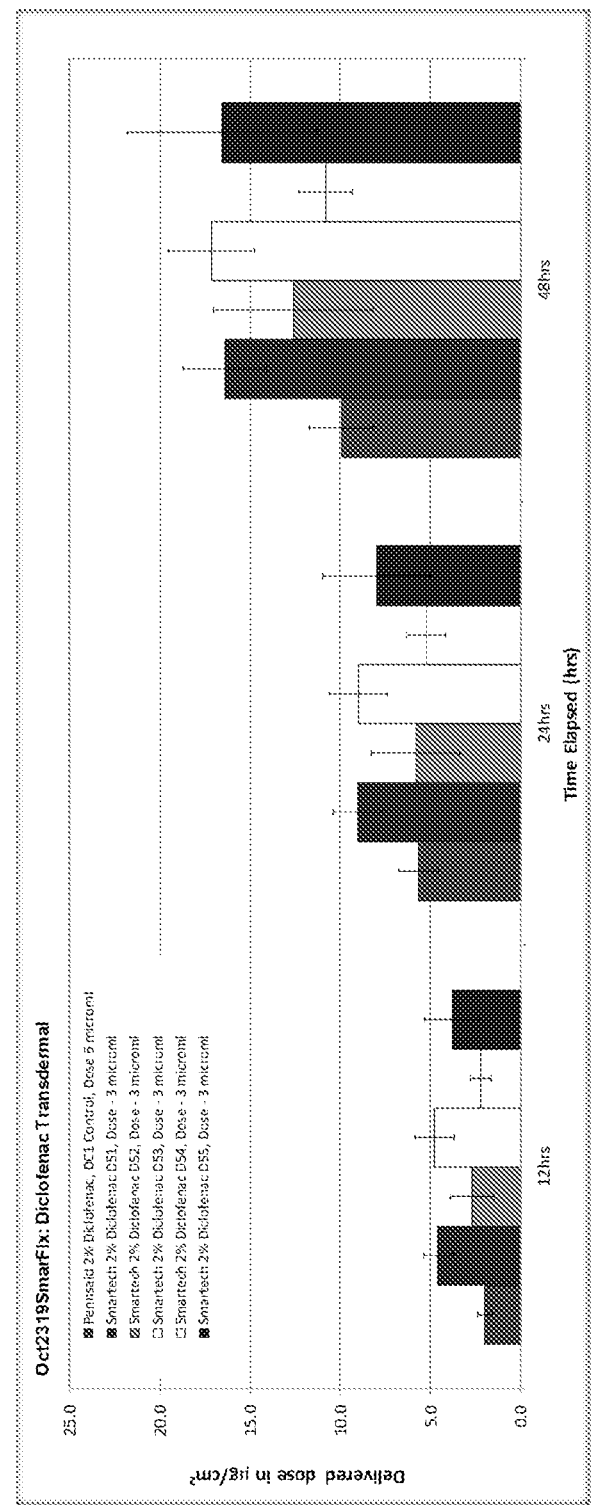
FIG. 12: delivered transdermal dose data for 2% diclofenac formulations D51-D55 and Pennsaid.

In FIG. 12, bar 1: Pennsaid 2% Diclofenac, DC1 Control, Dose 6 μL; bar 2, 2% Diclofenac D51, Dose-3 μL; bar 3 2% Diclofenac D52, Dose-3 μL; bar 4 2% Diclofenac D53, Dose-3 μL; bar 4, 2% Diclofenac D53; bar 5, 2% Diclofenac D54; bar 6, 2% Diclofenac D55.

Figure 13:
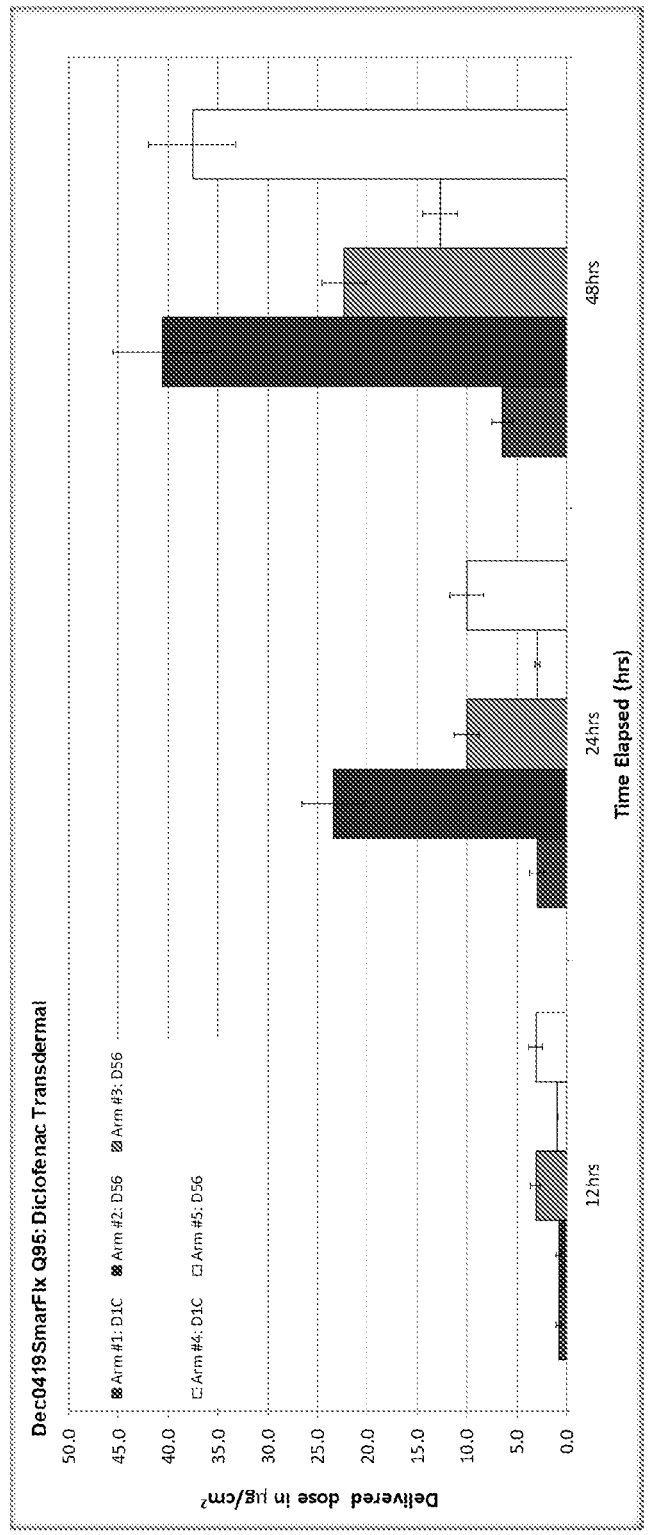
FIG. 13: delivered transdermal dose data for 2% diclofenac formulation D56 and Pennsaid.

In FIG. 13, Arm #1 DIC Pennsaid Dose 6 μL; Arm #2 D56 Dose 6 μL; Arm #3 D56 Dose 3 μL; Arm #4 D1C Pennsaid Apply Another 6 μL Dose at 24 hrs.; Arm #5 D56 Apply Another 3 μL Dose at 24 hrs.

Cadaver skin permeation data shows the 2% diclofenac permeation in both the Pennsaid (6 μL dose) and Formula D56 (3 μL dose) products into the epidermis and dermis, and through the cadaver skin sample. The following calculations show the amount of sodium diclofenac that would remain on a cm² of skin surface after 48 hours for these formulations. As shown, nearly seven times more sodium diclofenac would remain on the skin surface/cm² for the Pennsaid product compared to the Formula D56 which, for a topical prescription drug, could potentially be a concern for the consumer applying repeated daily doses.

Example 7

Additional formulations which vary the amounts of oleic acid, propylene glycol, and ethyl alcohol were examined by the same procedure.

| Ingredient | Formula D1C PENNSAID 2% Diclofenac Wt % | Formula D57 Wt % | Formula D58 Wt % | Formula D59 Wt % |
|---|---|---|---|---|
| Oleic Acid | 0 | 0 | 0 | 0 |
| Glycerin | 0 | 0 | 4.0 | 0 |
| DMSO | 45.5 | 20.0 | 20.0 | 20.0 |
| Transcutol | 0 | 24.5 | 24.5 | 24.5 |
| Sodium Diclofenac | 2.0 | 2.0 | 2.0 | 2.0 |
| Propylene Glycol | 11.0 | 11.0 | 11.0 | 11.0 |
| Ethyl Alcohol Dehydrated | 31.35 | 39.5 | 35.5 | 35.5 |
| Hydroxypropyl Cellulose | 3.0 | 3.0 | 3.0 | 3.0 |
| Water | 7.15 | 0 | 0 | 0 |
| Oleyl Alcohol | 0 | 0 | 0 | 4.0 |
| TOTAL | 100 | 100 | 100 | 100 |

In these formulations there was no Oleic Acid added to the formulation. In formulation D58 glycerin was added at 4.0%. In formulation D59 Oleyl Alcohol was added at 4.0%.

Without the Oleic Acid in the formulation, the permeation of diclofenac diminished significantly to the point where the permeation was less than Pennsaid. Oleic Acid and Oleyl Alcohol enhance penetration of diclofenac.

Figure 14:
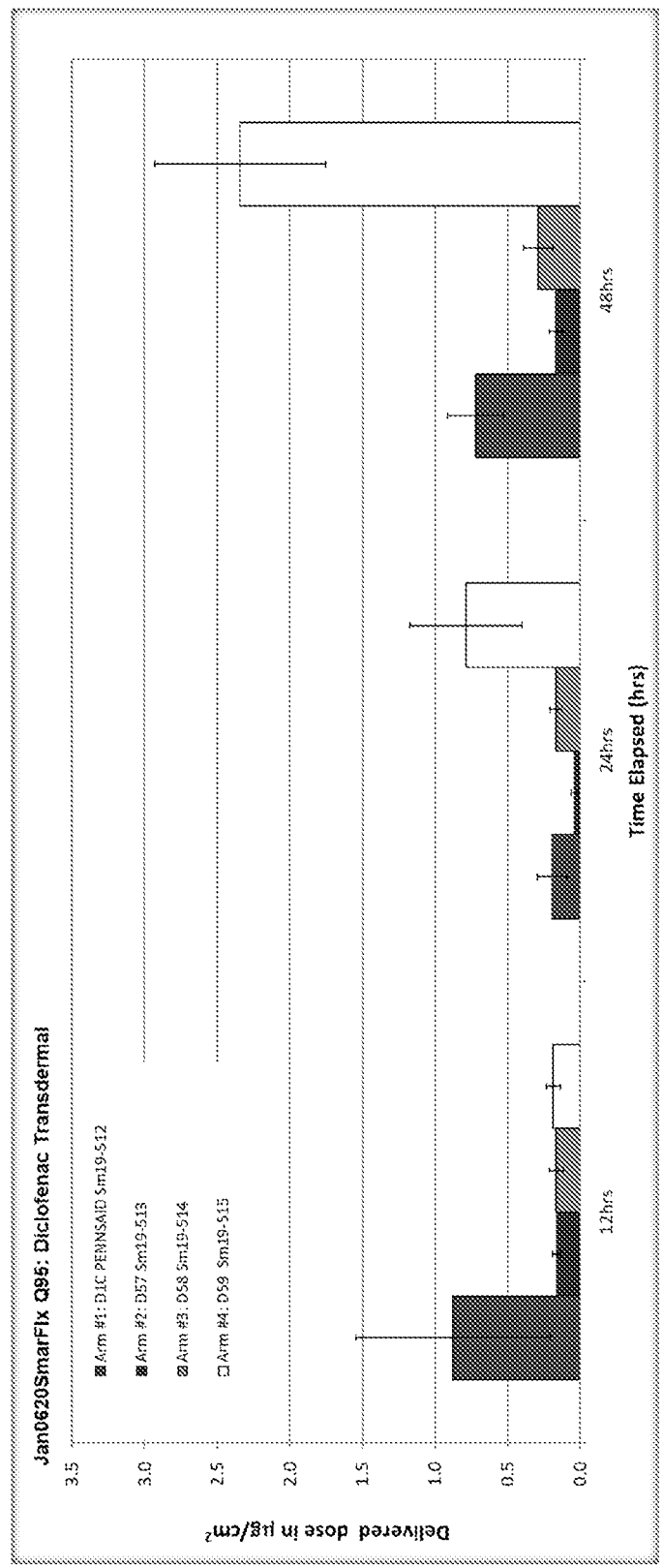
FIG. 14: delivered transdermal dose data for 2% diclofenac formulation D57-D59 and Pennsaid.

In FIG. 14, Arm #1 DIC Pennsaid; Arm #2 D57; Arm #3 D58; Arm #4 D59.

Example 8: Publications

The following publications are herein incorporated by reference in their entirety.

McPherson and Cimino, Topical NSAID Formulations, Pain Medicine, Volume 14, Issue suppl_1, Dec. 2013, Pages S35-S39, doi.org/10.1111/pme.12288

|  | Diclofenac Dose | Penetration Into Epidermis | Penetration Into Dermis | Penetration Through Skin | TOTAL μg Diclofenac Penetrating Into and Through the Skin | TOTAL μg Diclofenac Remaining on the Skin Surface |
|---|---|---|---|---|---|---|
| Pennsaid | 6 μL (120 μg) | 11 μg | 1 μg | 7 μg | 19 μg | 101 μg |
| D56 | 3 μL (60 μg) | 21 μg | 2 μg | 22 μg | 45 μg | 15 μg |

WO2009081217
WO2016033308
WO2017173269
U.S. 9101591

One skilled in the art readily appreciates that the present disclosure is well adapted to carry out the objects and obtain the ends and advantages mentioned, as well as those inherent therein. The examples provided herein are representative of preferred embodiments, are exemplary, and are not intended as limitations on the scope of the disclosure.

It will be readily apparent to a person skilled in the art that varying substitutions and modifications may be made to the disclosure disclosed herein without departing from the scope and spirit of the disclosure.

All patents and publications mentioned in the specification are indicative of the levels of those of ordinary skill in the art to which the disclosure pertains. All patents and publications are herein incorporated by reference to the same extent as if each individual publication was specifically and individually indicated to be incorporated by reference.

The disclosure illustratively described herein suitably may be practiced in the absence of any element or elements, limitation or limitations that is not specifically disclosed herein. Thus, for example, in each instance herein any of the terms "comprising", "consisting essentially of" and "consisting of" may be replaced with either of the other two terms. The terms and expressions that have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

Other embodiments are set forth within the following claims.

I claim:

1. A topical Diclofenac formulation, wherein the formulation is anhydrous and consists of:
   1.8 to 2.2 wt % Diclofenac;
   28.35 to 34.65 wt % anhydrous ethanol;
   7.2 to 8.8 wt % oleic acid, oleyl alcohol, or a mixture thereof;
   9.9 to 12.1 wt % propylene glycol;
   2.7 to 3.3 wt % hydroxypropylcellulose;
   18 to 22 wt % dimethylsulfoxide; and
   22.05 to 26.95 wt % 2-(2-Ethoxyethoxy)ethanol.

2. A topical Diclofenac formulation of claim 1, wherein the amount of Diclofenac is 2 wt %.

3. A topical Diclofenac formulation of claim 2, wherein the formulation consists of
   2 wt % Diclofenac;
   31.5 wt % anhydrous ethanol;
   8 wt % oleic acid or oleyl alcohol;
   11 wt % propylene glycol;
   3 wt % hydroxypropylcellulose;
   20 wt % dimethylsulfoxide; and
   24.5 wt % 2-(2-Ethoxyethoxy)ethanol.

4. A topical Diclofenac formulation of claim 2, wherein the formulation consists of
   2 wt % Diclofenac;
   29 wt % anhydrous ethanol;
   8 wt % oleic acid or oleyl alcohol;
   11 wt % propylene glycol;
   3 wt % hydroxypropylcellulose;
   21 wt % dimethylsulfoxide; and
   26 wt % 2-(2-Ethoxyethoxy)ethanol.

5. A method of topically treating a pain episode at a location on the human body, comprising topically applying a topical Diclofenac formulation according to claim 1 to the location.

6. A method of topically treating a pain episode at a location on the human body, comprising topically applying a topical Diclofenac formulation according to claim 2 to the location.

7. A method of topically treating a pain episode at a location on the human body, comprising topically applying a topical Diclofenac formulation according to claim 3 to the location.

8. A method of topically treating a pain episode at a location on the human body, comprising topically applying a topical Diclofenac formulation according to claim 4 to the location.

* * * * *